(12) United States Patent
Zinger et al.

(10) Patent No.: US 7,632,261 B2
(45) Date of Patent: Dec. 15, 2009

(54) FLUID TRANSFER DEVICE

(75) Inventors: Freddy Zinger, Ra'anana (IL); Igor Denenburg, Rehovot (IL)

(73) Assignee: Medimop Medical Projects, Ltd., Ra'anana (IL)

( * ) Notice: Subject to any disclaimer, the term of this patent is extended or adjusted under 35 U.S.C. 154(b) by 168 days.

(21) Appl. No.: 11/694,297

(22) Filed: Mar. 30, 2007

(65) Prior Publication Data

US 2007/0167904 A1 Jul. 19, 2007

Related U.S. Application Data

(60) Continuation of application No. 10/062,796, filed on Jan. 31, 2002, now Pat. No. 7,326,194, which is a continuation-in-part of application No. 09/633,056, filed on Aug. 8, 2000, now Pat. No. 6,379,340, which is a division of application No. 08/913,432, filed as application No. PCT/US96/03732 on Mar. 19, 1996, now Pat. No. 6,238,372, which is a continuation of application No. 08/499,213, filed on Jul. 7, 1995, now abandoned, and a continuation-in-part of application No. 08/407,287, filed on Mar. 20, 1995, now abandoned.

(30) Foreign Application Priority Data

Aug. 16, 1995 (IL) ..................................... 114960

(51) Int. Cl.
*A61B 19/00* (2006.01)
(52) U.S. Cl. ..................... 604/414; 604/411; 604/412; 604/413
(58) Field of Classification Search ................ 604/126, 604/190, 403, 405, 406, 411–415, 537, 539; D24/129, 130; 215/247, 249
See application file for complete search history.

(56) References Cited

U.S. PATENT DOCUMENTS 3,484,849 A 12/1969 Huebner et al.

(Continued)

FOREIGN PATENT DOCUMENTS

DE 41 22 476 T1 1/1993

(Continued)

OTHER PUBLICATIONS

Novel Transfer, Mixing and Drug Delivery Systems, MOP Medimop Medical Projects, Ltd. Catalog, 4 pages, Rev. 4, 2004.

(Continued)

*Primary Examiner*—Nicholas D Lucchesi
*Assistant Examiner*—Victoria P Campbell
(74) *Attorney, Agent, or Firm*—Panitch Schwarze Belisario & Nadel LLP

(57) ABSTRACT

A fluid ducting assembly enables flow communication between a syringe and one of a vessel and a dispenser for dispensing a fluid contained therein. The fluid ducting assembly includes a base having first, second, and third members for connection to and providing flow communication with the syringe, the vessel and the dispenser, respectively. The fluid ducting assembly further includes a flow controller within the base enabling a flow path between the first and second members or between the first and third members. The flow controller has a first operative position in which the flow path between the first and second members is enabled or a second operative position in which the flow path between the first and third members is enabled. The flow controller is readily switchable from its first to its second operative position but not readily switchable from its second to its first operative position.

3 Claims, 25 Drawing Sheets

U.S. PATENT DOCUMENTS

| | | |
|---|---|---|
| 3,618,637 A | 11/1971 | Santomieri |
| 3,757,981 A | 9/1973 | Harris, Sr. et al. |
| 3,826,261 A | 7/1974 | Killinger |
| 3,885,607 A | 5/1975 | Peltier |
| 3,957,052 A | 5/1976 | Topham |
| 3,977,555 A | 8/1976 | Larson |
| 3,993,063 A | 11/1976 | Larrabee |
| 4,020,839 A | 5/1977 | Klapp |
| 4,051,852 A | 10/1977 | Villari |
| 4,253,501 A | 3/1981 | Ogle |
| D271,421 S | 11/1983 | Fetterman |
| 4,434,823 A | 3/1984 | Hudspith |
| 4,564,054 A | 1/1986 | Gustavsson |
| 4,588,396 A | 5/1986 | Stroebel et al. |
| 4,604,093 A | 8/1986 | Brown et al. |
| 4,607,671 A | 8/1986 | Aalto et al. |
| 4,614,437 A | 9/1986 | Buckler |
| 4,638,975 A | 1/1987 | Iuchi et al. |
| 4,639,019 A | 1/1987 | Mittleman |
| 4,697,622 A | 10/1987 | Swift et al. |
| 4,721,133 A | 1/1988 | Sundblom |
| 4,743,229 A | 5/1988 | Chu |
| 4,758,235 A | 7/1988 | Tu |
| 4,759,756 A | 7/1988 | Forman et al. |
| 4,787,898 A | 11/1988 | Raines |
| 4,967,797 A | 11/1990 | Manska |
| 4,997,430 A | 3/1991 | Van Der Heiden et al. |
| 5,049,129 A | 9/1991 | Zdeb et al. |
| 5,088,996 A | 2/1992 | Kopfer et al. |
| 5,104,387 A | 4/1992 | Pokorney et al. |
| 5,113,904 A | 5/1992 | Askanian |
| 5,201,705 A | 4/1993 | Berglund et al. |
| 5,203,771 A | 4/1993 | Melker et al. |
| 5,211,638 A | 5/1993 | Dudar et al. |
| 5,269,768 A | 12/1993 | Cheung |
| 5,270,219 A | 12/1993 | DeCastro et al. |
| 5,279,576 A | 1/1994 | Loo et al. |
| 5,288,290 A | 2/1994 | Brody |
| 5,334,163 A | 8/1994 | Sinnett |
| 5,342,346 A | 8/1994 | Honda et al. |
| 5,350,372 A | 9/1994 | Ikeda et al. |
| 5,385,547 A | 1/1995 | Wong et al. |
| 5,466,220 A | 11/1995 | Brenneman |
| 5,478,337 A | 12/1995 | Okamoto et al. |
| 5,520,659 A | 5/1996 | Hedges |
| 5,526,853 A | 6/1996 | McPhee |
| 5,566,729 A | 10/1996 | Grabenkort et al. |
| 5,573,281 A | 11/1996 | Keller |
| 5,636,660 A | 6/1997 | Pfleiderer et al. |
| 5,641,010 A | 6/1997 | Maier |
| 5,653,686 A | 8/1997 | Coulter et al. |
| 5,743,312 A | 4/1998 | Pfeifer et al. |
| 6,063,068 A | 5/2000 | Fowles et al. |
| D427,308 S | 6/2000 | Zinger |
| 6,080,132 A | 6/2000 | Cole et al. |
| 6,139,534 A | 10/2000 | Niedospial, Jr. et al. |
| 6,156,025 A | 12/2000 | Niedospial et al. |
| 6,238,372 B1 | 5/2001 | Zinger et al. |
| 6,474,375 B2 | 11/2002 | Spero et al. |
| D495,416 S | 8/2004 | Dimeo et al. |
| 2003/0153895 A1 | 8/2003 | Leinsing |

FOREIGN PATENT DOCUMENTS

| | | |
|---|---|---|
| DE | 195 04 413 T1 | 8/1996 |
| EP | 0 192 661 B1 | 9/1986 |
| EP | 0 195 018 B1 | 9/1986 |
| EP | 0 258 913 A2 | 3/1988 |
| EP | 0416454 B1 | 3/1991 |
| EP | 0521460 B1 | 1/1993 |
| EP | 0 814 866 B1 | 1/1998 |
| EP | 0 898 951 A2 | 3/1999 |
| EP | 1 329 210 A1 | 7/2003 |
| EP | 1 454 609 A1 | 9/2004 |
| EP | 1 454 650 A1 | 9/2004 |
| WO | WO 96/29113 A1 | 9/1996 |
| WO | WO 2005/105014 A1 | 11/2005 |

OTHER PUBLICATIONS

Smart Site® Alaris Medical Systems Product Brochure, 4 pages, Issue 1, Oct. 1999.

Smart Site® Needle-Free Systems, Alaris Medical Systems Webpage, 4 pages, Feb. 2006.

Photographs of Alaris Medical Systems SmartSite® device, 5 pages, 2002.

Non-Vented Vial Access Pin with Ultrasite® Valve, B. Braun Medical, Inc. website and product description, 3 pages, Feb. 2006.

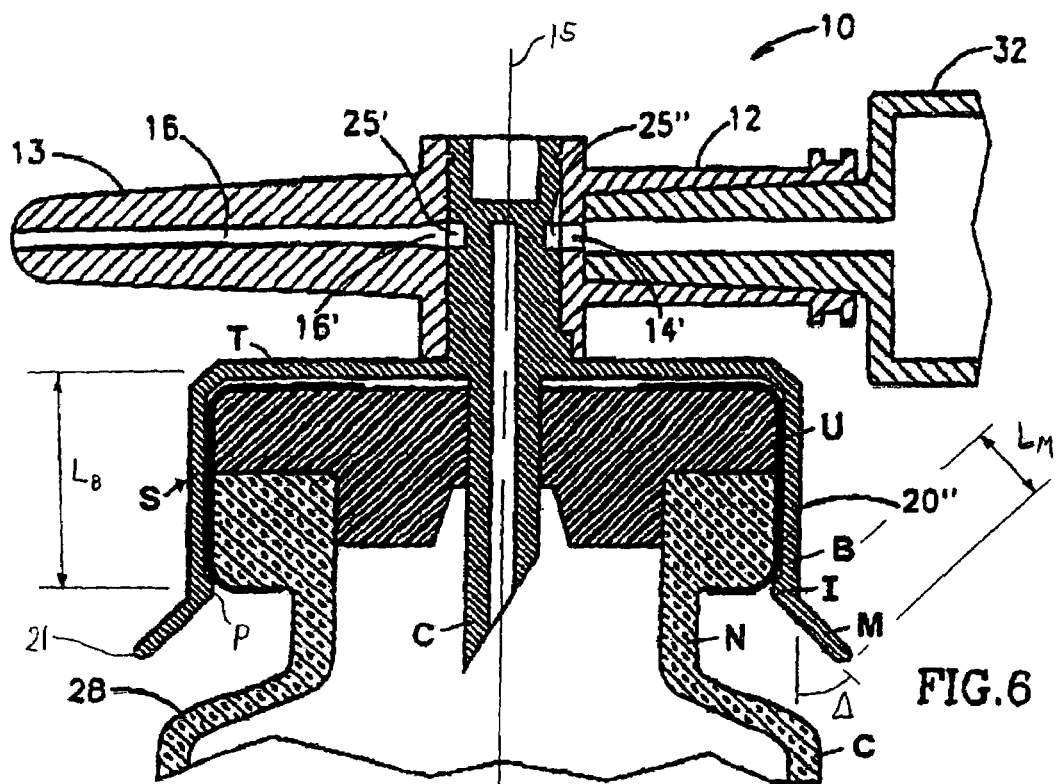
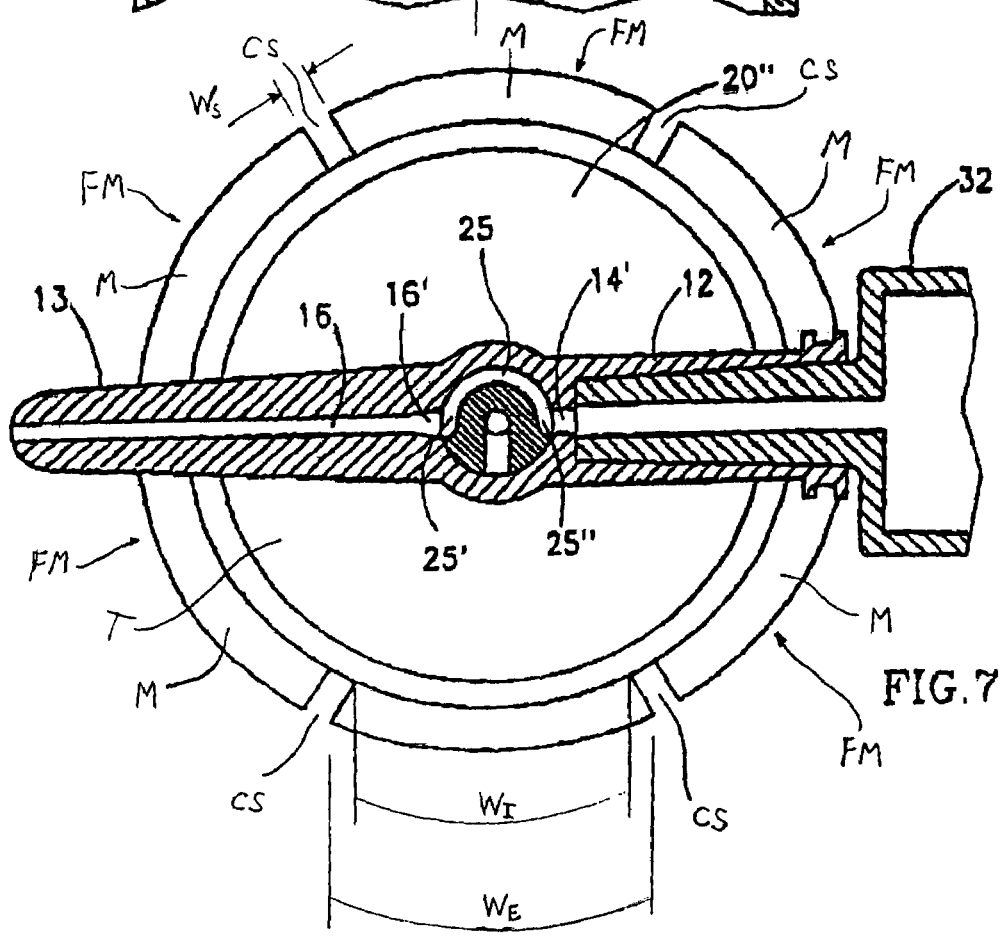

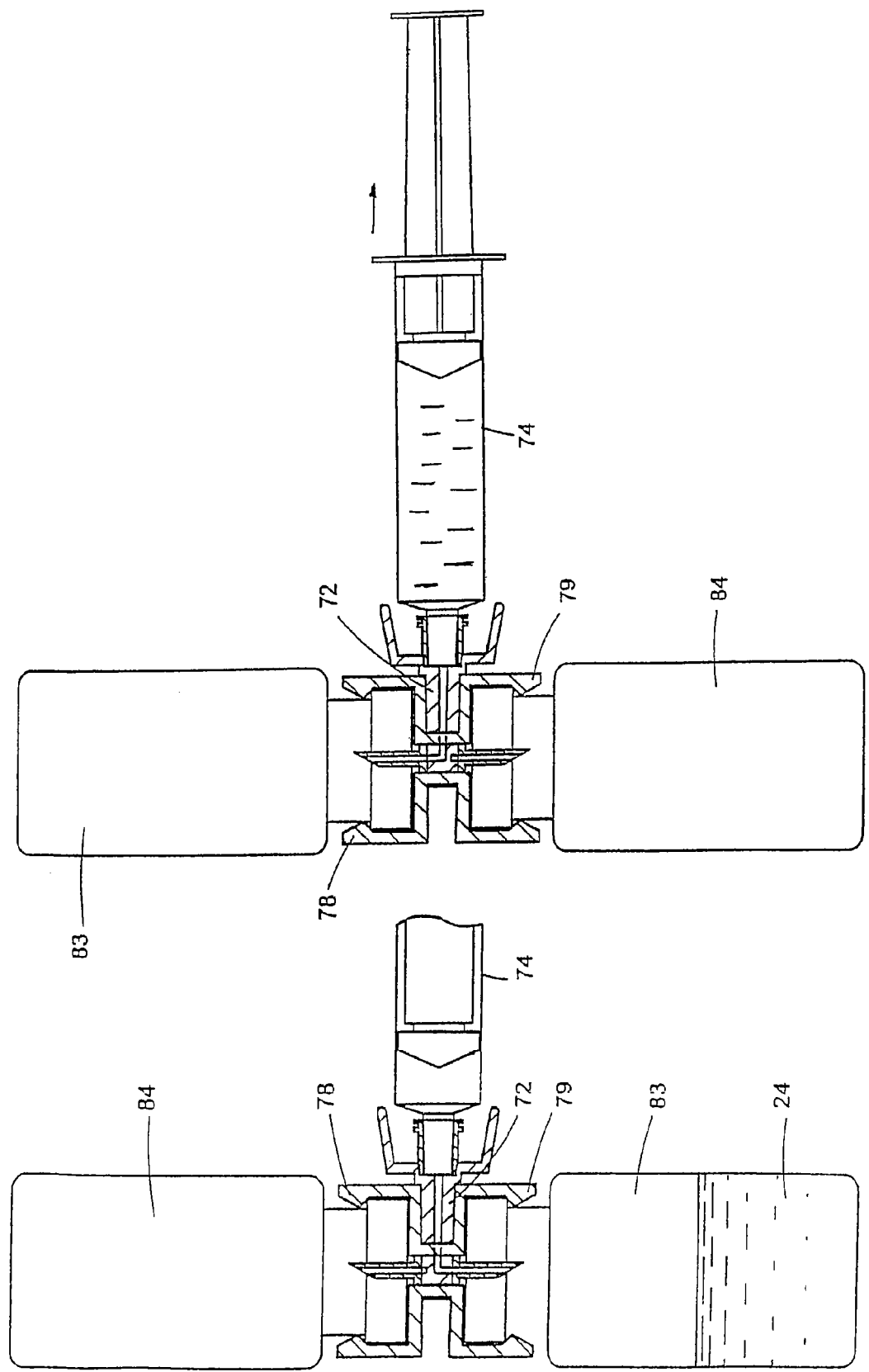

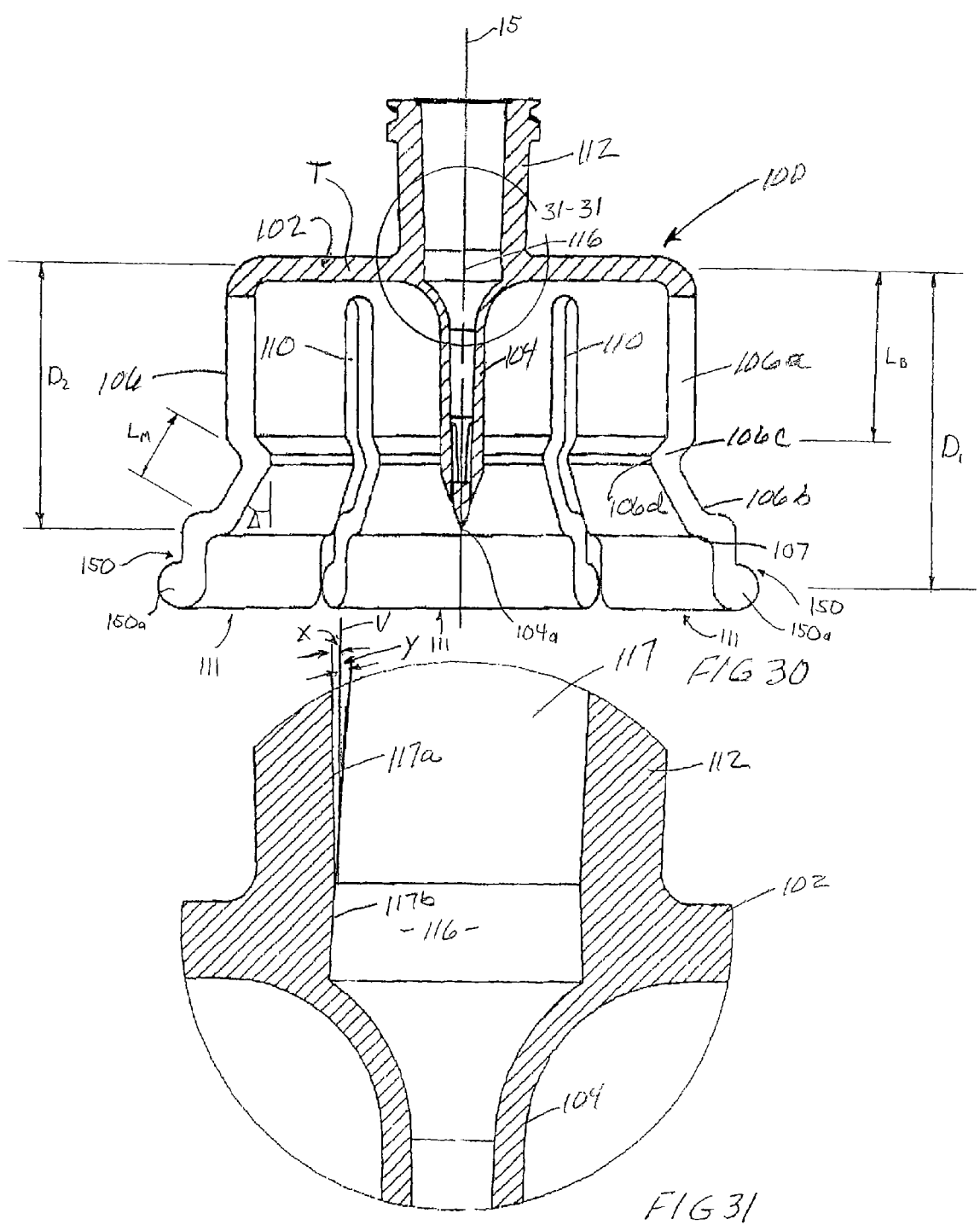

FLUID TRANSFER DEVICE

CROSS-REFERENCE TO RELATED APPLICATIONS

This patent application is a continuation of U.S. patent application Ser. No. 10/062,796, filed Jan. 31, 2002, which is a continuation-in-part of U.S. patent application Ser. No. 09/633,056, now U.S. Pat. No. 6,379,340 B1, filed Aug. 8, 2000, which is a divisional of U.S. patent application Ser. No. 08/913,432, now U.S. Pat. No. 6,238,372 B1, filed Sep. 17, 1997, which is a 371 National Phase application based on International Application No. PCT/US96/03732, which claims priority to U.S. patent application Ser. No. 08/499,213, filed Jul. 7, 1995, now abandoned, and U.S. patent application Ser. No. 08/407,287, filed Mar. 20, 1995, now abandoned.

BACKGROUND OF THE INVENTION

Drugs intended for parenteral administration are typically stored in a medicinal vessel either as a dry powder or as a solution. The solution can be ready for immediate use or in the form of a liquid concentrate which requires reconstitution with a physiological solution prior to administration in a similar manner to a dry powder drug. The physiological solution can be provided in a pre-filled syringe or a medicinal vessel.

Medicinal vessels typically fall into one of three categories. The first type is a vial or a glass bottle closed by a rubber stopper which can be penetrated by a puncturing tool, for example, a needle, and which is self-closing upon withdrawal of the puncturing tool. Such a vial or glass bottle can contain a single dose or a multiple dose of a drug. The drug contained in a vial can be under a high vacuum. The second type is an ampoule whose top portion is broken off enabling access to its contents. The third type is an IV bag provided with a sample port for enabling access to its contents. The sample port can be of the pre-slit septum type.

Regardless of the manner in which a drug is stored, there is a need to transfer fluid under sterile conditions before its administration to a patient by a dispensing tool be it a needle, a pre-slit septum, or the like. When a prior dilution of a drug is required, the process requires at least two fluid transfers. The problem of ensuring proper fluid transfer under aseptic conditions is especially acute in the case of Self-administration of drugs by patients in their homes.

Assemblies which have hitherto been proposed for the aseptic administration of drugs are described in U.S. Pat. No. Des. 271,421, U.S. Pat. Nos. 3,618,637, 3,757,981, 3,826,261, 3,957,052, 3,977,555, 3,993,063, 4,051,852, 4,564,054, 4,604,093, 4,721,133, 4,758,235, 4,967,797, 4,997,430, 5,201,705, 5,269,768, 5,279,576, 5,288,290, 5,334,163, and 5,466,220, and European Publication Nos. 0 258 913 A2, 0 195 018 B1, 0 192 661 B1, and 0 416 454 B1.

In particular, EP 0 521 460 B1 describes a fluid control device for use with a syringe and a pair of medicinal vessels. The fluid control device includes a housing with a luer-connector port for receiving the syringe and second and third ports each comprising an adaptor having a fluid conduit member extending into the interior of a medicinal vessel when attached thereto. In the housing, a flow control member is slidingly displaceable from a first flow control position enabling a flow path between the two medicinal vessels when connected and a second flow control position enabling a flow path between one of the medicinal vessels and the syringe.

BRIEF SUMMARY OF THE INVENTION

Briefly stated, the present invention is directed to a fluid transfer device the object of which is to provide fluid control devices enabling the aseptic administration of drugs.

In accordance with the invention, there is provided a fluid transfer device for use with a syringe and at least one medicinal vessel. The fluid transfer device includes a first port, a second port for receiving the syringe, a third port comprising an adaptor having a fluid conduit member extending into the interior of the medicinal vessel when attached thereto and a flow control member selectively disposable from a first flow control position enabling a flow path between a first pair of two ports and a second flow control position enabling a flow path between a second pair of two ports. The flow control member is coupled to one of the ports for manipulation between said flow control positions.

In accordance with the teachings of the present invention, there is provided a family of fluid control devices which are adapted for the aseptic administration of drugs either directly or indirectly to a patient. The selection of the most suitable fluid control device depends on the type of drug to be administered to a patient, the manner in which it is packaged, the manner in which it is to be administered to a patient and by whom apart from other factors. Some of the devices are designed to enable the reconstitution of a drug provided in a powder form or as a liquid concentrate. Some of the devices are suited for vials or ampoules containing a single dose of a drug whilst others are suited for vials or IV bags containing multiple doses.

In a preferred embodiment of a fluid control device, the flow control member is rotatably mounted in a body member so as to be selectively rotatable between its first flow control position and its second flow control position.

In a preferred embodiment of a fluid control device, the first port is adapted for dispensing a drug directly or indirectly to a patient and, as such it can be provided with a needle, it can be fashioned as a male luer connector on which a needle can be mounted or it can be fashioned as a plastic cannula for insertion into a pre-slit septum. In such an embodiment, the adaptor is preferably coupled to a flow control member adapted for rotation in a body member having the port adapted for receiving a syringe and the dispensing port.

The adaptor can be integrally formed with the flow control member and designed so as to readily broken off therefrom after rotation of the flow control member from its first flow control position to its second flow control position. Alternatively, the adaptor can be detachably engaged to the flow control member by means of an interengaging means enabling axial detachment of the adaptor from the body member on a relative rotation therebetween to a position which urges the flow control member from its first flow control position to its second flow control position.

In a preferred embodiment of a fluid control device suitable for use with drugs which require reconstitution, the fluid control device includes a fourth port in the form of an adaptor for enabling the attachment of a second medicinal vessel to the body member.

In a preferred embodiment of a fluid control device, the first port is also provided with an adaptor adapted for attachment thereto of a medicinal vessel and, in this case, the port adapted for receiving the syringe is rotatably coupled to the flow control member.

In each case, the adaptor can be adapted for attachment thereto of a vial, an ampoule or an IV bag, the former requiring that the fluid conduit member be formed as a puncturing tool for piercing the vial's rubber stopper on its attachment thereto. In the case of attachment of an ampoule, because the ampoule cannot be inverted, the fluid conduit member is required to be provided as a long straw to enable all or nearly all of its contents to be aspirated therefrom.

The adaptor can also include a conduit for venting the vessel when attached thereto. The conduit can include a filter for filtering the air traversing therethrough. The filter can be deployed within a lateral cavity provided within the adaptor or, alternately, the filter can be provided as a discrete element exterior to the fluid control device.

BRIEF DESCRIPTION OF THE SEVERAL VIEWS OF THE DRAWINGS

For a better understanding of the present invention and to show how the same may be carried out in practice, and solely by way of non-limiting examples, reference will now be made to the accompanying drawings, in which:

FIG. 6 is a vertical cross sectional view of the fluid control device of FIG. 1 along the line A-A after rotation of the adaptor relative to the base member;

FIG. 7 is a horizontal cross sectional view of the fluid control device of FIG. 1 along the line B-B after rotation of the adaptor relative to the base member;

FIG. 30 is a side-elevational view, partly in cross section of an alternate form of adapter component of the present invention;

FIG. 31 is a greatly enlarged, cross-sectional view of the area designated 31-31 in FIG. 30;

DETAILED DESCRIPTION OF THE INVENTION

Figure 1:
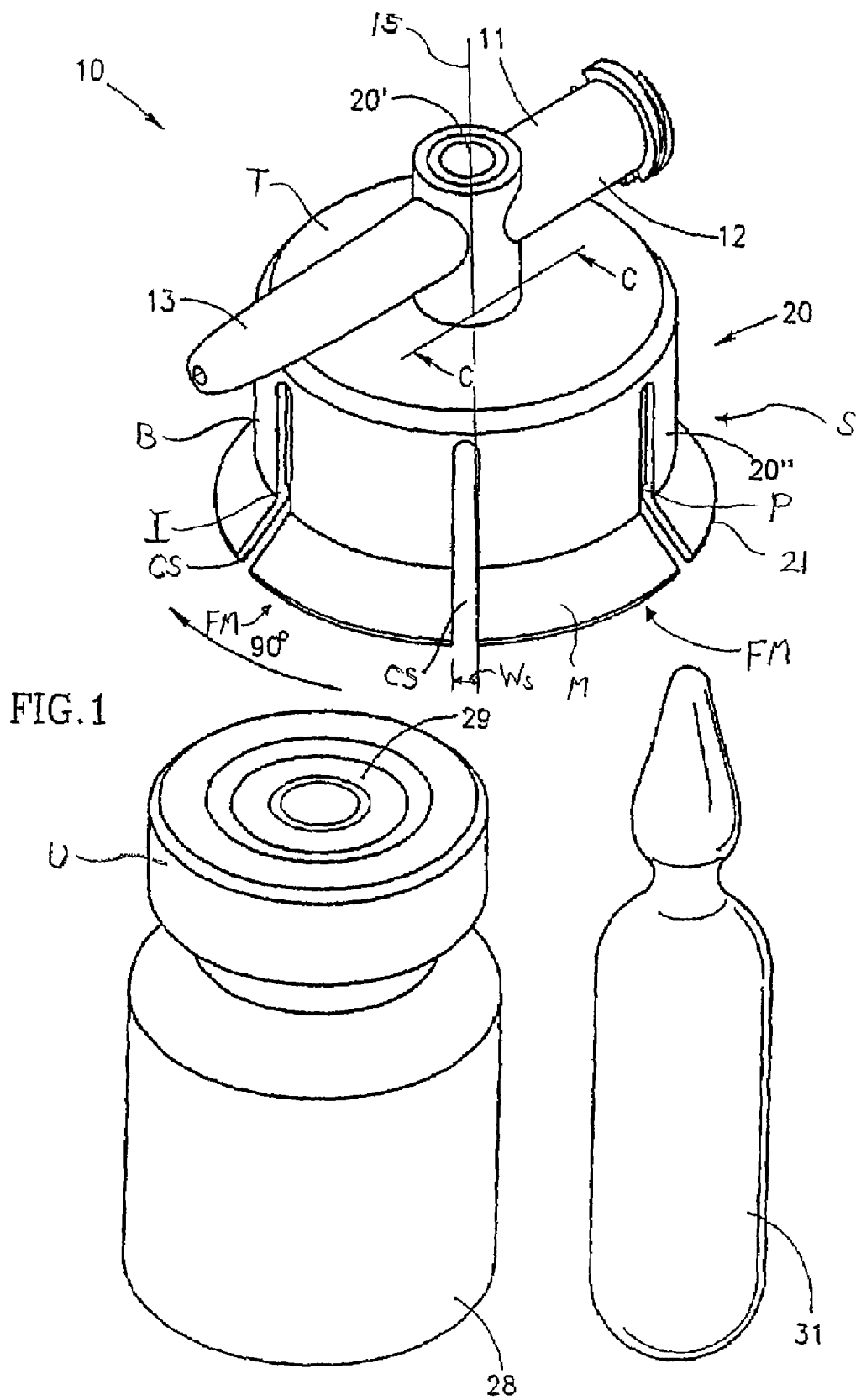
FIG. 1 is a perspective view of an assembled fluid control or fluid transfer device including a base member and an integrally formed adaptor cum flow control member for use with a syringe and a medicinal vessel.

FIGS. 1-8 depict a first embodiment of a fluid control or fluid transfer device, generally designated 10, constructed and operative in accordance with the teachings of the present invention for enabling fluid flow control between a syringe 32, a medicinal vessel 28 and a dispensing port 13. The fluid transfer device 10 includes an elongated base member 11 having a port 12 adapted for receiving a syringe 32 and a dispensing port 13 fashioned as a plastic cannula for insertion into a pre-slit septum assembly known in the art per se. The port 12 is typically fashioned as a female Luer connector 12. The fluid transfer device 10 includes a longitudinal axis 15. As is understood by one having ordinary skill in the art, a fluid transfer device typically include a lumen connecting two ports, while a fluid control device typically includes a flow control member for diverting flow between at least two flow paths, however, these terms are not meant to be limiting.

Figure 3:
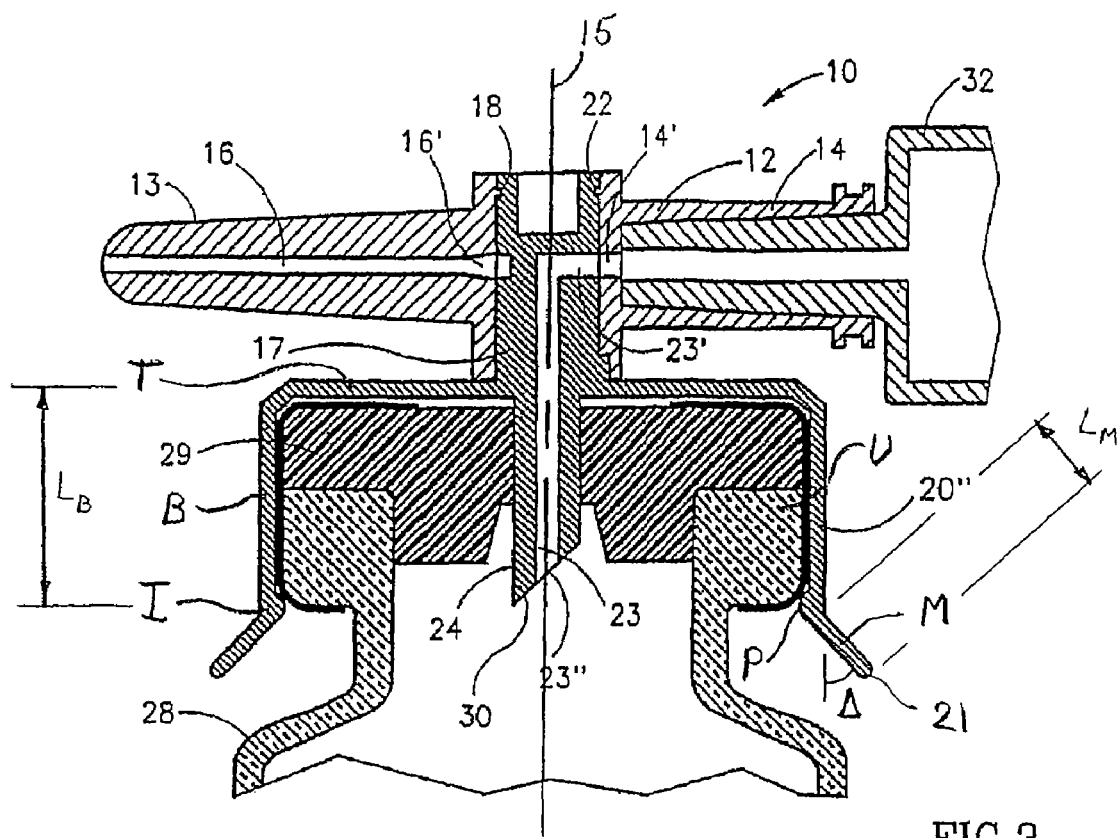
FIG. 3 is a vertical cross sectional view of the fluid control device of FIG. 1 along the line A-A after insertion of a syringe and the attachment of a vial and before rotation of the adaptor relative to the base member.

As shown in FIG. 3, the port 12 includes a lumen 14 having an interior opening 14' and the dispensing port 13 includes a lumen 16 having an interior opening 16'. The lumens 14 and 16 are co-axial and in flow communication via a bore 17 transversely disposed relative to the elongated base member 11. The bore 17 includes an upper peripheral flange 18 and a lower minor peripheral abutment wall portion 19 protruding radially inward relative to its major peripheral wall portion 19' (see FIG. 5). As shown, the abutment wall portion 19' typically extends through an arc angle of about ninety degrees (90°).

The fluid control device 10 further includes an integrally formed adaptor and flow control member, generally designated 20, for insertion into the bore 17 in which it is restrained therein by means of a peripherally formed groove 22 designed for receiving the flange 18 therein. The flow control member 20' is formed with two flow ducts as follows: a first flow duct 23 (see FIG. 3) in the form of an L-shaped channel having a radial aperture 23' for registration with the interior opening 14' and an axial aperture 23' of a fluid conduit member 24 integrally formed as part of the adaptor 20" on disposition of the flow control member 20' in a first flow control position enabling flow communication between a syringe inserted in the port 12 and a vessel attached to the adaptor 20". A second flow duct 25 (see FIG. 4) in the form of a peripheral slightly longer than a semi-circular groove 25 having a first end portion 25' for registration with one of the interior openings 14' and 16' and a second end portion 25" for registration with the other of the interior openings 14' and 16' on disposition of the flow control member 20' in a second flow control position enabling flow communication between a syringe inserted in the port 12 and the dispensing port 13.

Figure 5:
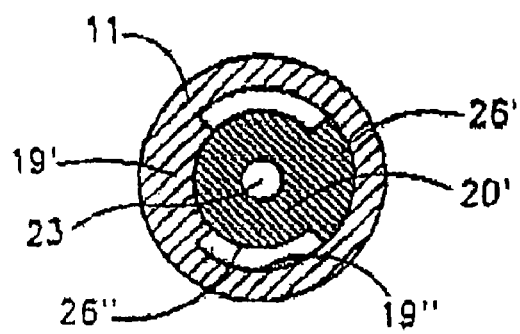
FIG. 5 is a horizontal cross sectional view of the fluid control device of FIG. 1 along the line C-C before rotation of the adaptor relative to the base member.

In addition, the flow control member 20' is provided with a minor peripheral abutment wall portion 26' protruding radially outward relative to its major peripheral wall portion 26" (see FIG. 5). As shown, the abutment wall portion 26' typically extends through an arc angle of about ninety degrees (90°). The minor peripheral abutment wall portions 19' and 26' are so disposed such that they assume substantially diagonally opposing positions relative to one another (see FIG. 5) in the first flow control position of the flow control member 20'.

Figure 2:
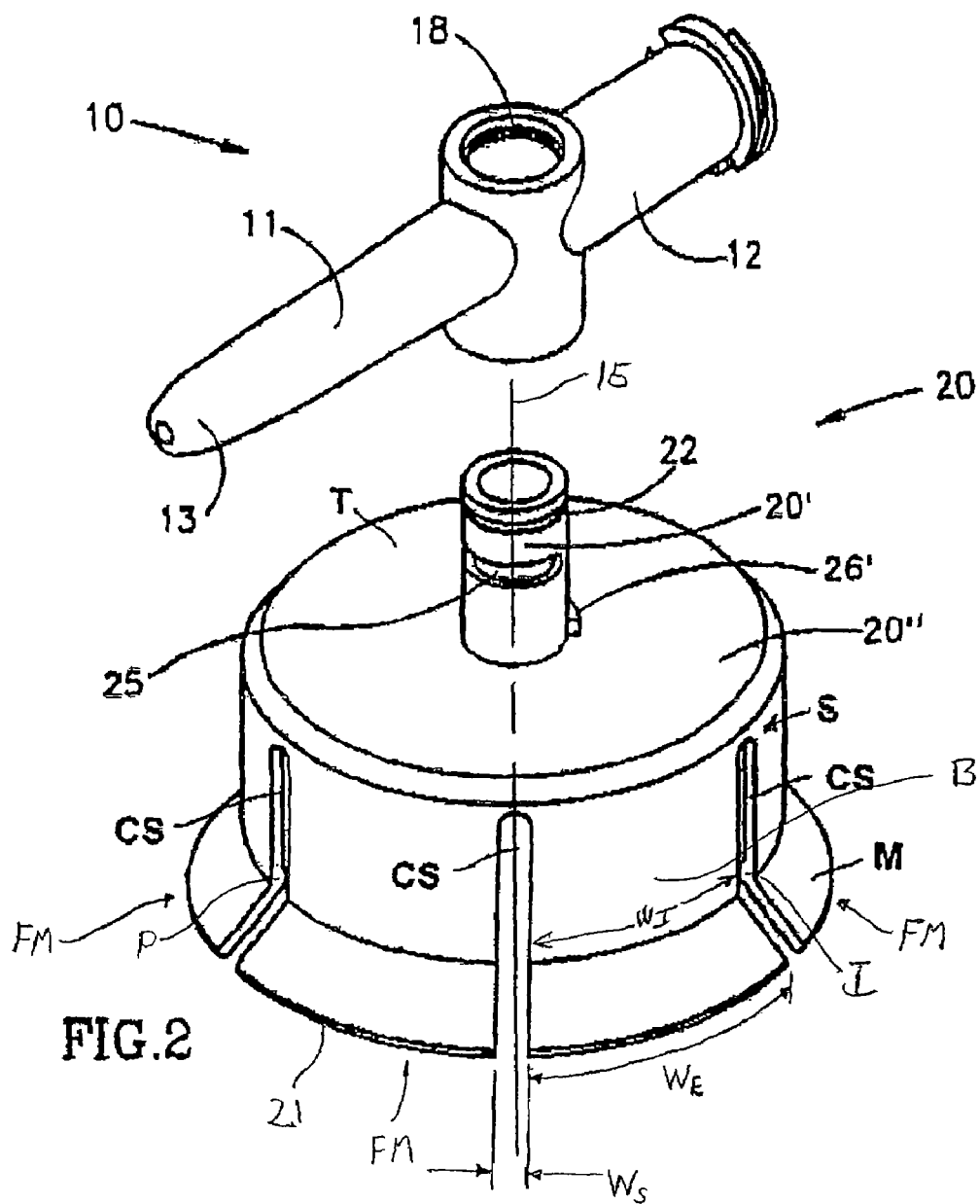
FIG. 2 is a perspective view of the fluid control device of FIG. 1 before assembly.

The adaptor 20" is shown to be adapted for the attachment thereto of a vial 28 (not drawn to size) provided with a rubber stopper 29. As shown in FIG. 6, the vial 28 has a container portion C and an intermediate neck portion N. As shown in FIGS. 2 and 6, the adaptor 20" has a top T and a resiliently deformable skirt S connected to top wall T and extending therefrom for telescopically receiving the upper portion U of the vial 28. As best seen in FIG. 6, the skirt S has a generally cylindrical body portion B, an angularly outwardly extending marginal portion M, and an angularly inwardly extending intermediate portion I disposed between the body portion B and the outwardly extending marginal portion M for releasably gripping the vial 28. The outwardly extending marginal portion M has a distal end 21 and extends from the inwardly extending intermediate portion I at a guiding angle Δ. The guiding angle Δ may be measured between a marginal portion M and the body portion B or between the marginal portion M and the longitudinal axis 15. The intermediate portion I here comprises a circumferentially extending protuberance P. The adapter "20" also includes a hollow cannula C connected to the top wall T (see FIG. 6). Further, as shown in FIG. 2, the skirt S is provided with circumferentially spaced slits CS that define flex members FM therebetween. Referring now to FIG. 6, the outwardly extending marginal portion M has a length $L_M$ that is at least one-third (⅓) the length $L_B$ of the generally cylindrical body portion B.

Each stage of the two stage operation of the fluid control device 10 for the administration of a drug provided in powder form for dilution with a physiological solution provided in a pre-filled syringe is now described with reference to FIGS. 3-5 and FIGS. 6-8, respectively.

Figure 4:
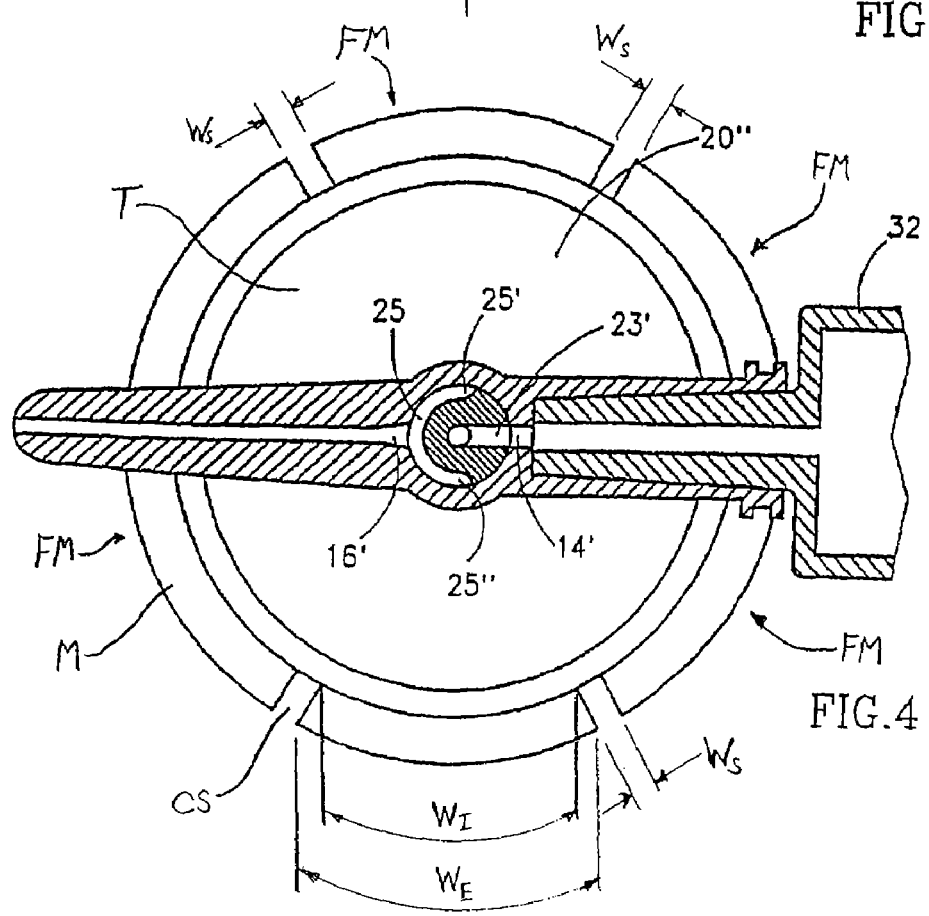
FIG. 4 is a horizontal cross sectional view of the fluid control device of FIG. 1 along the line B-B after insertion of a syringe and the attachment of a vial and before rotation of the adaptor relative to the base member.

As shown in FIGS. 3-5, the fluid control device 10 is best provided in a set-up position in which the flow control member 20' is in its first flow control position and the two minor abutment wall portions 19' and 26' are diagonally opposed to one another. As shown, it should be noted as best seen in FIG. 4, that the semi-circular groove 25 registers with the interior opening 16' but does not provide a flow path.

In this arrangement, a pre-filled syringe 32 is inserted into the port 12 and the vial 28 is attached to the adaptor 20" by means of which action, the puncturing tool 30 punctures the vial's rubber stopper 29, thereby enabling flow communication with its interior via the fluid conduit member 24. Typically, the syringe 32 requires actuation for expressing its contents into the vial 28 while in some cases, if the contents of the vial 28 are under vacuum, then the physiological solution of the syringe 32 can be sucked into the vial without user intervention. Thereafter, the contents of the vial 28 are shaken so as to reconstitute the powdered drug. The fluid control device 10 together with the vial 28 is then preferably inverted and the syringe 32 is aspirated so as to draw the reconstituted liquid drug therein.

Figure 8:
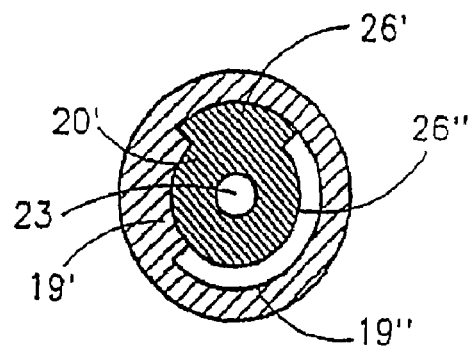
FIG. 8 is a horizontal cross sectional view of the fluid control' device of FIG. 1 along the line C-C before rotation of the adaptor relative to the base member.

Turning now to FIGS. 1, 2 and 6-8; the vial 28 together with the adaptor 20" are rotated in either a clockwise or a counter clockwise direction relative to the base member 11 until such time that abutment wall portion 26' is stopped by the abutment wall portion 19' (see FIG. 8). On rotation of the adaptor 20", the flow control member 20' is rotated to its second flow control position enabling a flow path between the syringe 32 and the dispensing port 13 by means of the end portions 25' and 25" of the semi-circular groove 25 registering with the interior openings 14' and 16'. The drug can then be dispensed by actuation of the syringe 32.

It can now be readily appreciated that the fluid control device 10 ensures that a drug can be administered to a patient under aseptic conditions. Furthermore, it can be readily appreciated that the fluid control device 10 presents a "foolproof" delivery device in the sense that a patient is required to perform a minimal number of actions to administer a drug and that the drug can only be dispensed in a single operative position of the fluid control device.

Figure 9:
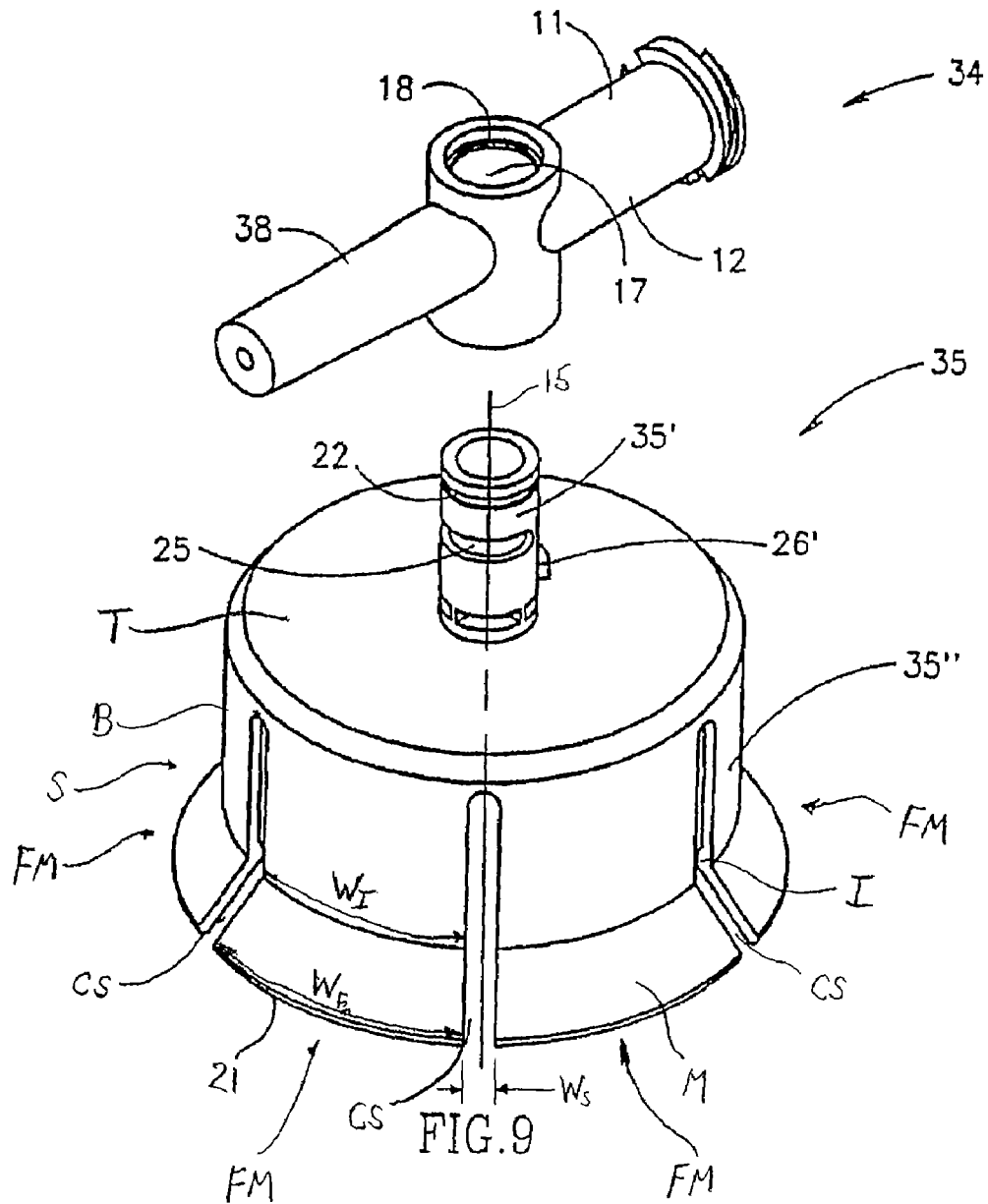
FIG. 9 is a perspective view of a modified integrally formed adaptor cum now control member adapted such that the adaptor breaks off from the flow control member on rotation of the adaptor relative to the base member beyond a pre-determined position.
Figure 10:
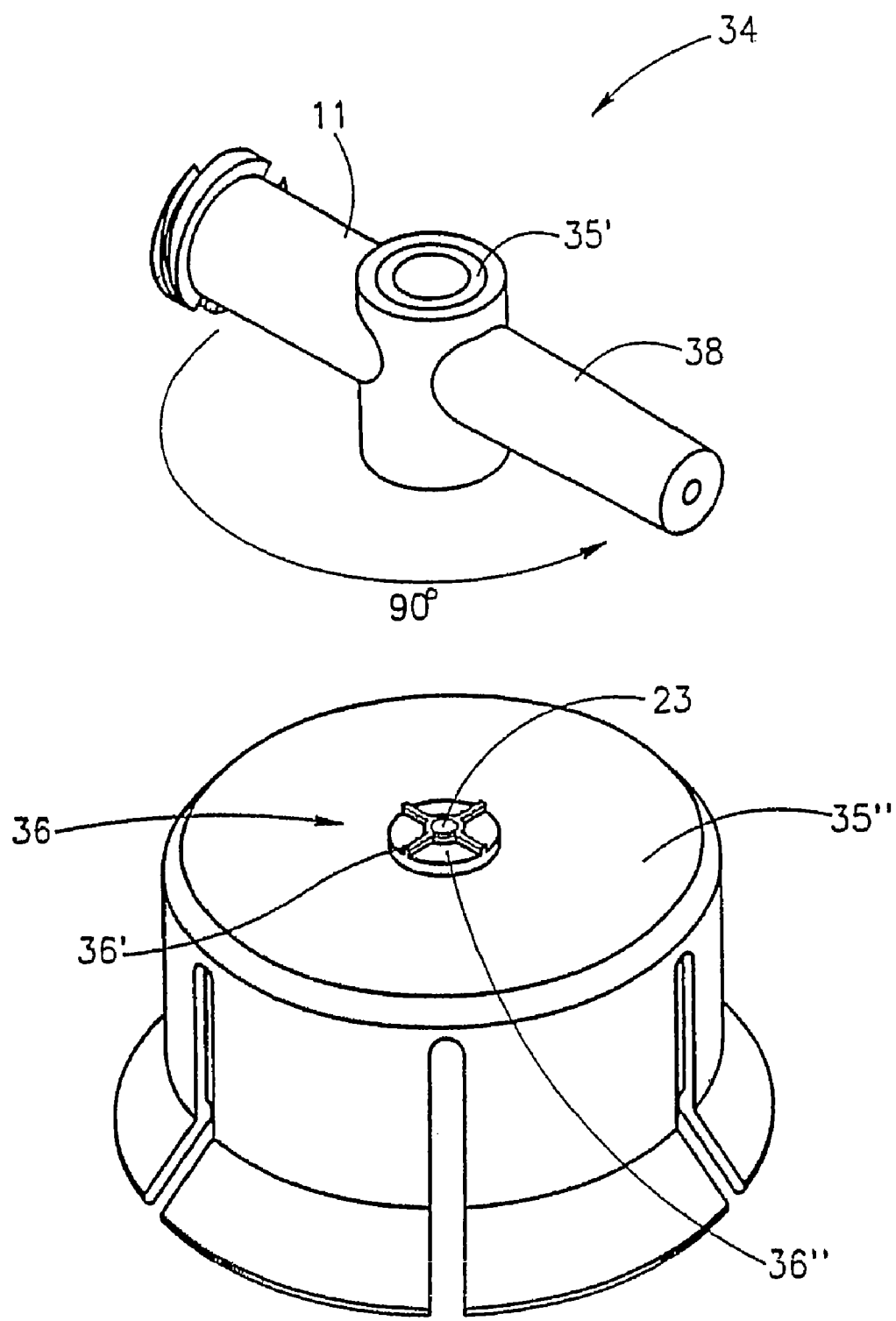
FIG. 10 is a perspective view of a fluid control device including the modified adaptor cum flow control member of FIG. 9 after the adaptor has been broken off.
Figure 11:
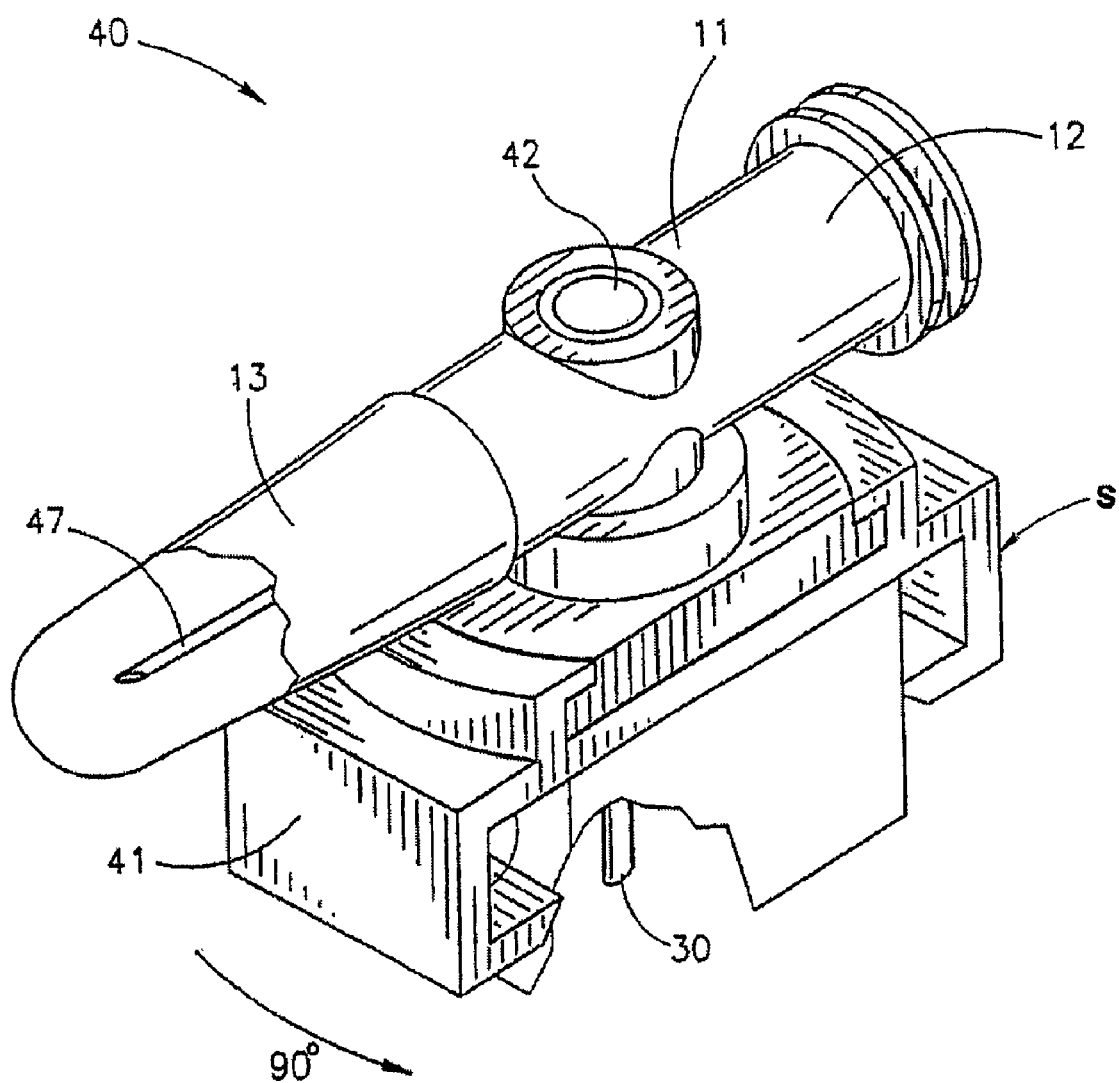
FIG. 11 is a perspective view of an assembled fluid control device including a base member and an adaptor designed for releasable engagement with the base member.
Figure 12:
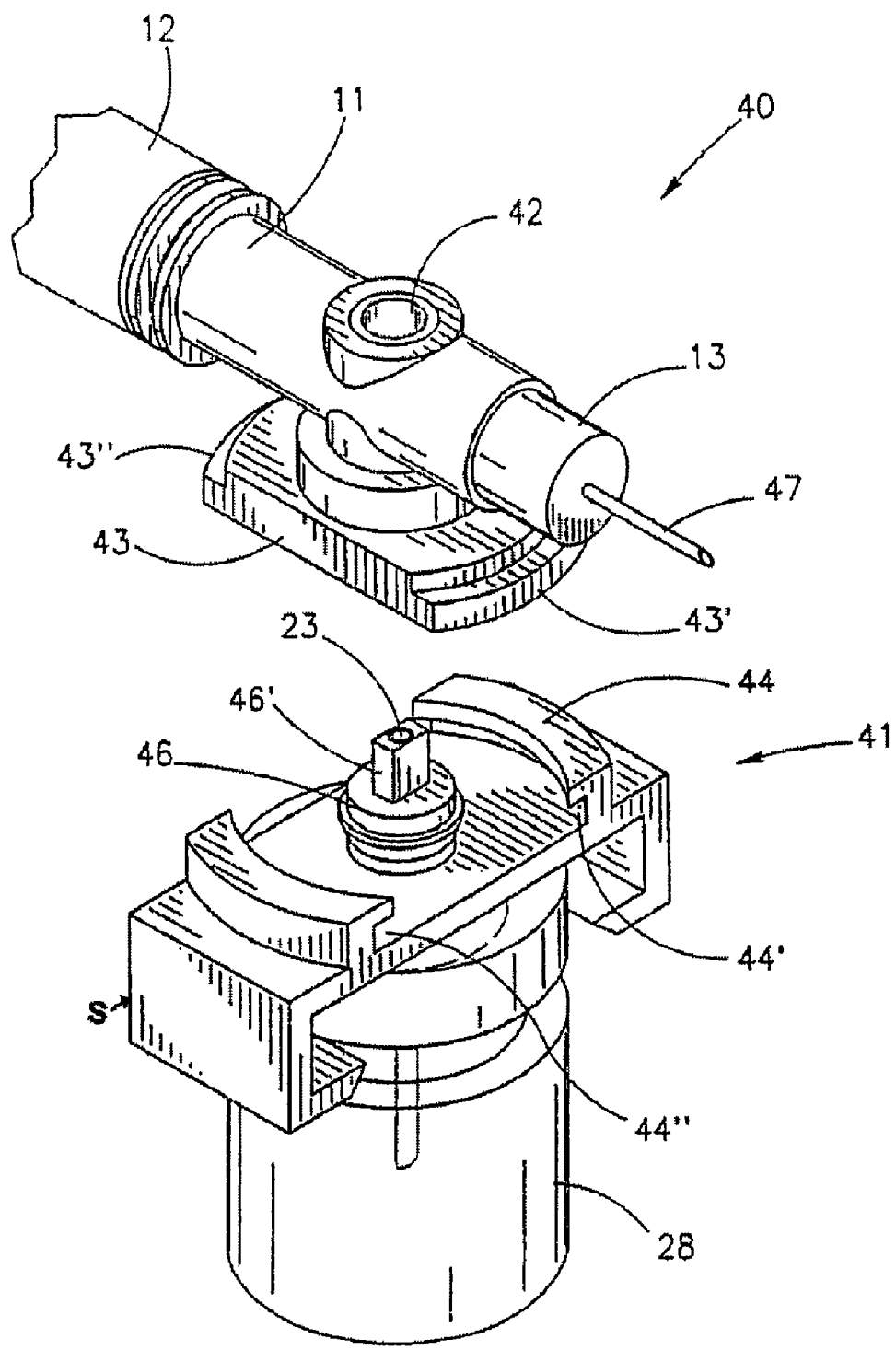
FIG. 12 is a perspective view of the fluid control device of FIG. 11 after the adaptor has been rotated through a quarter turn ready for its detachment from the base member.

FIGS. 9 and 10 depict a second embodiment of a fluid control or transfer device, generally designated 34, constructed and operative in accordance with the teachings of the present invention for enabling fluid flow control between a syringe, a medicinal vessel and a dispensing port. The fluid control device 34 is similar in construction and operation to the fluid control device 10 and therefore the same reference numbers are used where appropriate.

The main difference between the two fluid control devices 34 and 10 resides in the fact that the former includes an integrally formed adaptor cum flow control member 35 provided with a weakened portion, generally designated 36, between its abutment wall portion 26' of its flow control member 35' and its adaptor 35". As shown, this weakened portion 36 is achieved by leaving radially extending vanes 36' formed by cut-outs 36".

The advantage of this design is that after rotation of the vial 28 (not shown) and the adaptor 35" through ninety degrees (90°) so as to rotate the flow control member 35' from its first flow control position to its second flow control position, any further torque applied will tend to snap off the adaptor 35" which can then be discarded together with the vial, thereby rendering a less cumbersome and lighter remaining assembly so as to facilitate the administration of a drug.

A further difference between the fluid control devices 10, 34 is that the former includes a dispensing port 38 fashioned as a male Luer connector.

Figure 13:
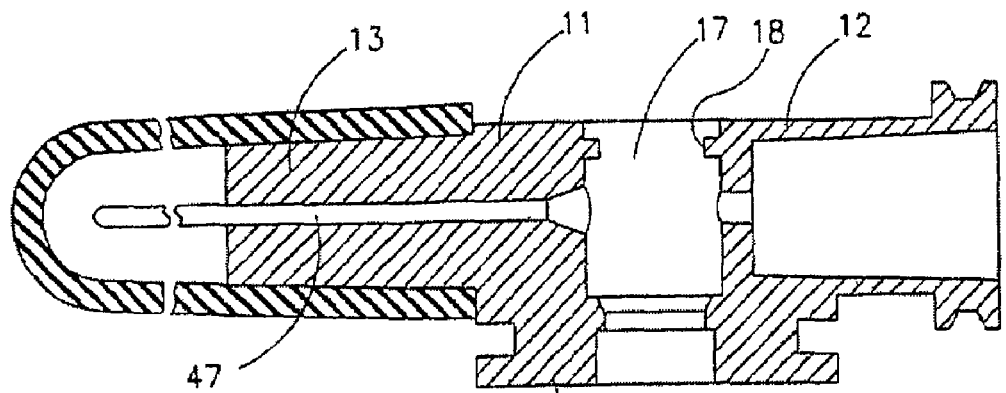
FIG. 13 is a vertical cross sectional view of the base member of the fluid control device of FIG. 11.
Figure 14:
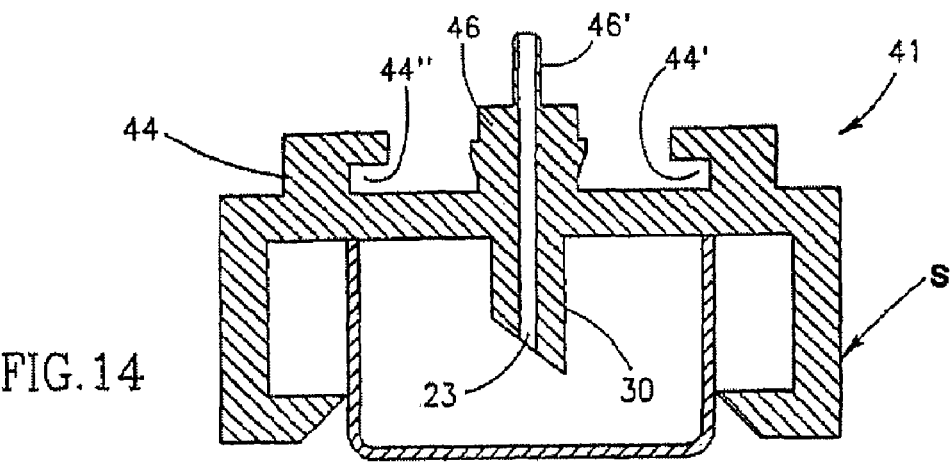
FIG. 14 is a vertical cross sectional view of the adaptor of the fluid control device of FIG. 11.
Figure 15:
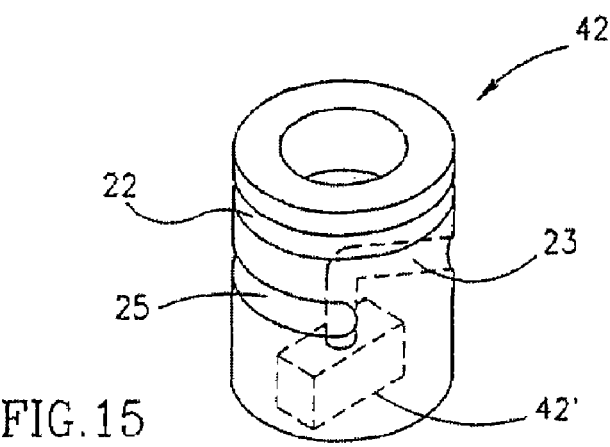
FIG. 15 is a perspective view of the flow control member of the fluid control device of FIG. 11.

FIGS. 13-15 depict a third embodiment of a fluid control device, generally designated 40, constructed and operative in accordance with the teachings of the present invention for enabling fluid flow control between a syringe, a medicinal vessel and a dispensing port. The fluid control device 40 is similar in construction and operation to the fluid control device 10 and therefore the same reference numerals are used where appropriate.

The main difference between the two fluid control devices 10, 40 is that the former includes an adaptor 41 designed for a non-destructive detachable engagement with a flow control member 42. As such, the base member 11 is provided with a downwardly depending rectangular shaped member 43 provided with outwardly extending flanges 43', 43" for engagement by an upwardly extending rectangular shaped grip 44 of the adaptor 41 provided with inwardly directed grooves 44', 44" for receiving the flanges 43', 43". In addition, the adaptor 41 is provided with an upwardly extending stem 46 provided with a rectangular-shaped key 46' for insertion into a similarly sized and shaped slot 42' formed in the underside of the flow control member 42.

In the fluid control device 40, the flow control member 42 is disposed in its first flow control position enabling a flow path between the port 12 and a medicinal vessel to be attached to the adaptor 41 when the adaptor 41 is mounted on the base member 11. Conversely, on the rotation of the adaptor 41 relative to the base member 11 to a position enabling axial detachment therefrom, the adaptor 41 urges the flow control member 42 from its first flow control position to its second flow control position enabling a flow path between the port 12 and the dispensing port 13. Preferably, there is a screw thread engagement between the base member 11 and the adaptor 41 designed such that there is an axial displacement of the adaptor 41 away from the base member 11 when it is rotated from its engaging position to its disengaging position.

It can be readily appreciated that the advantage of this design over the design of the fluid control device 34 while retaining all the advantages of the latter resides in the fact that the former is reusable after sterilization while the latter can only be used once due to the destruction of the adaptor cum flow control member 35. The adaptor cum flow control member 35 includes the top T, the skirt S with the body portion B and outwardly extending marginal portion M and the slits CS that define the flex members FM. Referring to FIGS. 1, 2, 4, 7 and 9, the adaptors 20", 35 include six (6) slits CS that define six (6) flex members FM.

Referring to FIGS. 2, 4 and 7, at least one of the flex members FM has an intermediate circumferential width $W_I$ defined between the at least two slits CS proximate the intermediate portion I and an end circumferential width $W_E$ defined between the at least two slits CS proximate the distal end 21. The end circumferential width $W_E$ is greater than the intermediate circumferential width $W_I$ of flex member FM.

A further difference between the fluid control devices 40,10 resides in the fact that the fluid control device 10 shown in FIG. 1 includes a dispensing port 13 provided with a needle 47.

Figure 16A:
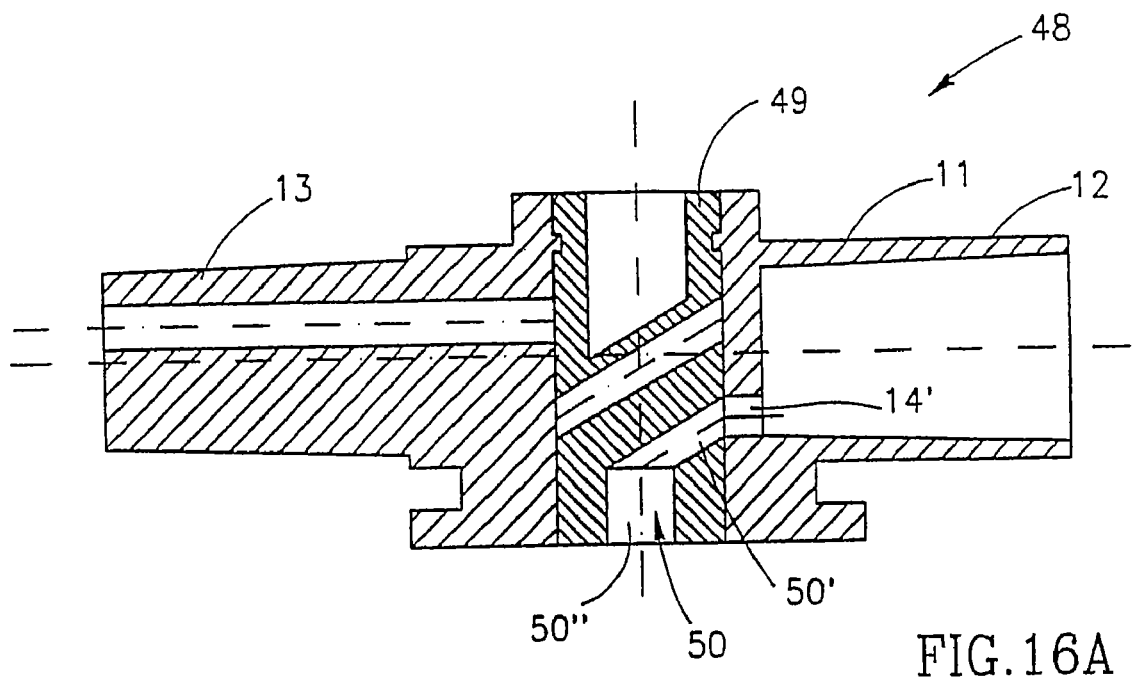
FIGS. 16A and 16B are vertical cross sectional views of a fluid control device in which the flow control member is required to be rotated through one hundred eighty degrees (180°) to enable switching between its flow control position.
Figure 16B:
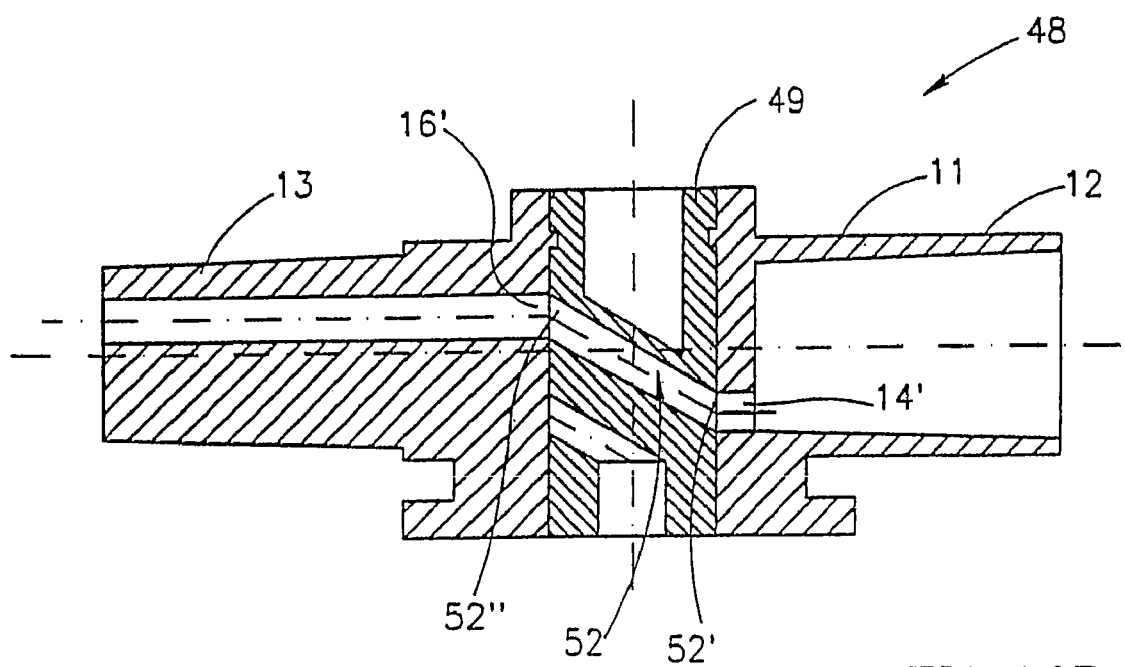

FIGS. 16A and 16B depict a fourth embodiment of a fluid control device, generally designated 48, constructed and operative in accordance with the teachings of the present invention for enabling fluid flow control between a syringe, a medicinal vessel and a dispensing port. The fluid control device 48 is similar in construction and operation to the fluid control device 41 and therefore the same reference numerals are used where appropriate.

The main difference between the two fluid control devices 48 and 41 resides in the fact that the former includes a flow control member 49 which is required to be rotated through a one hundred eighty degree (180°) turn between its first flow control position (see FIG. 16A) and its second flow control position (see FIG. 16B). In particular, the flow control member 49 includes an inclined channel 50 having a radial aperture 50' for registration with the interior opening 14' and an axial aperture 50" for registration with the fluid conduit member 24 so as to enable the flow path between a syringe and the interior of a medicinal vessel. The flow control member 49 includes a second inclined channel 52 having a radial aperture 52' for registration with the interior opening 14' and a radial aperture 52" for registration with the interior opening 16' so as to enable the flow path between a syringe to the dispensing port 13. As shown, in this case, the lumens 14 and 16 are not co-axial.

Figure 17:
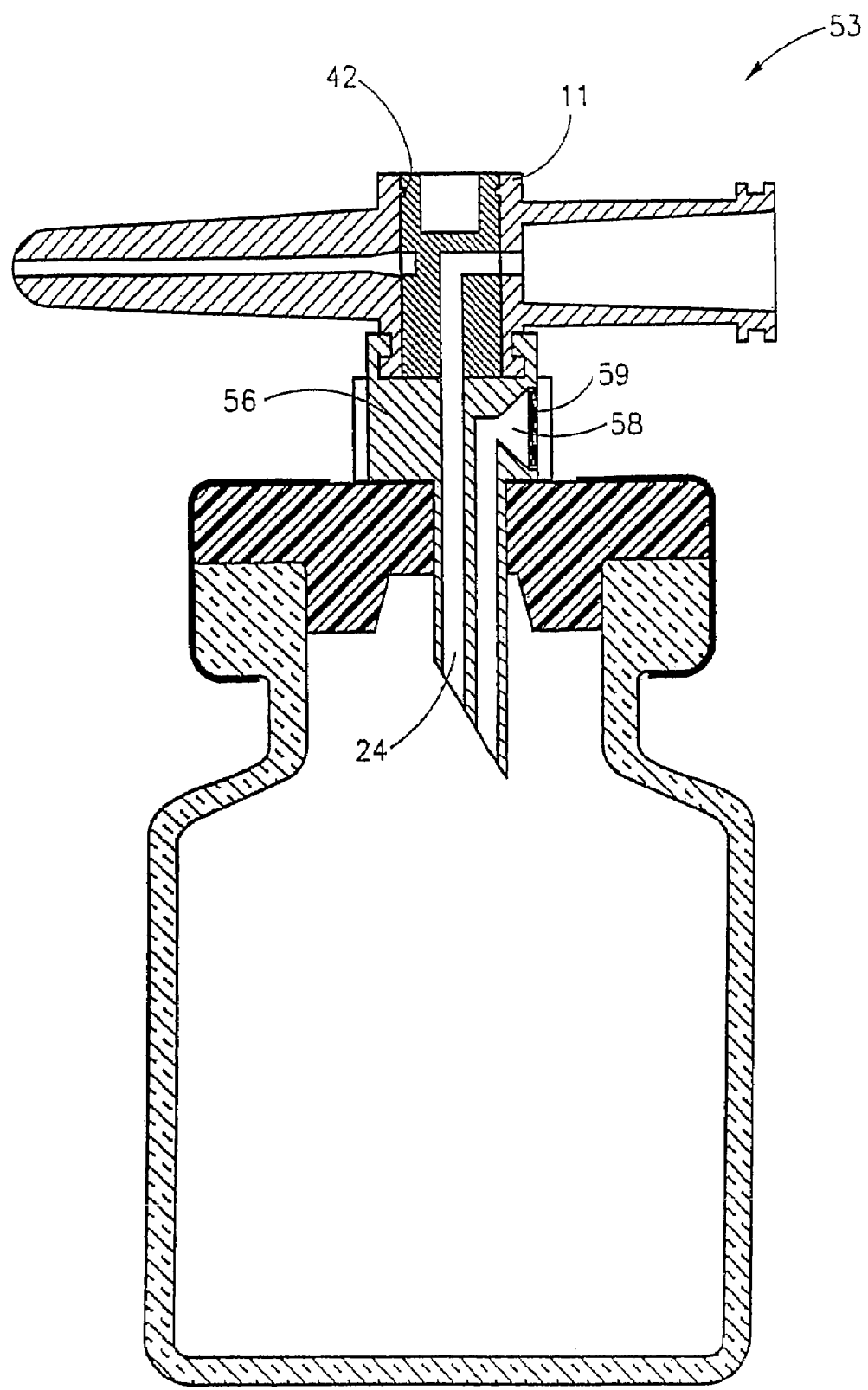
FIG. 17 is a vertical cross sectional view of a fluid control device provided with an arrangement for the venting of a vial attached to its adaptor.
Figure 18A:
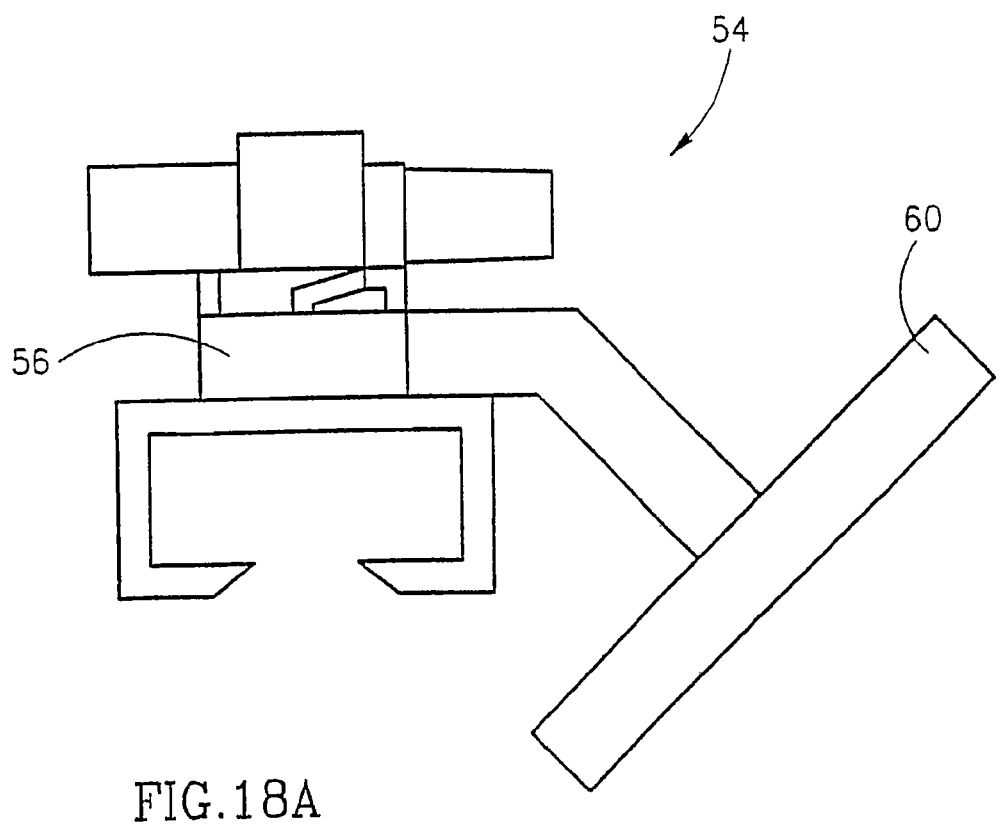
FIGS. 18A and 18B are two views depicting a fluid control device having a filter for filtering air venting a vial attached to its adaptor, the filter being provided as a discrete element exterior to the device.
Figure 18B:
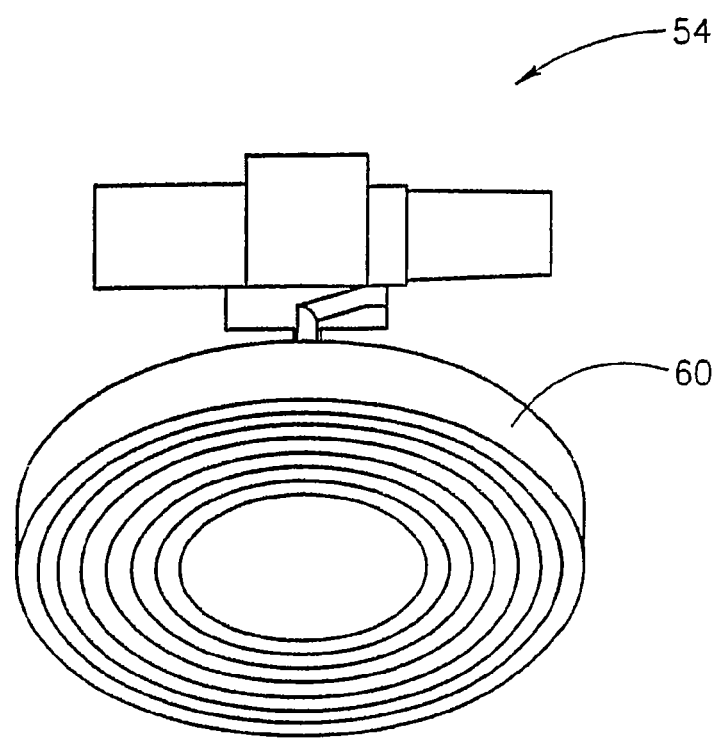
Figure 19:
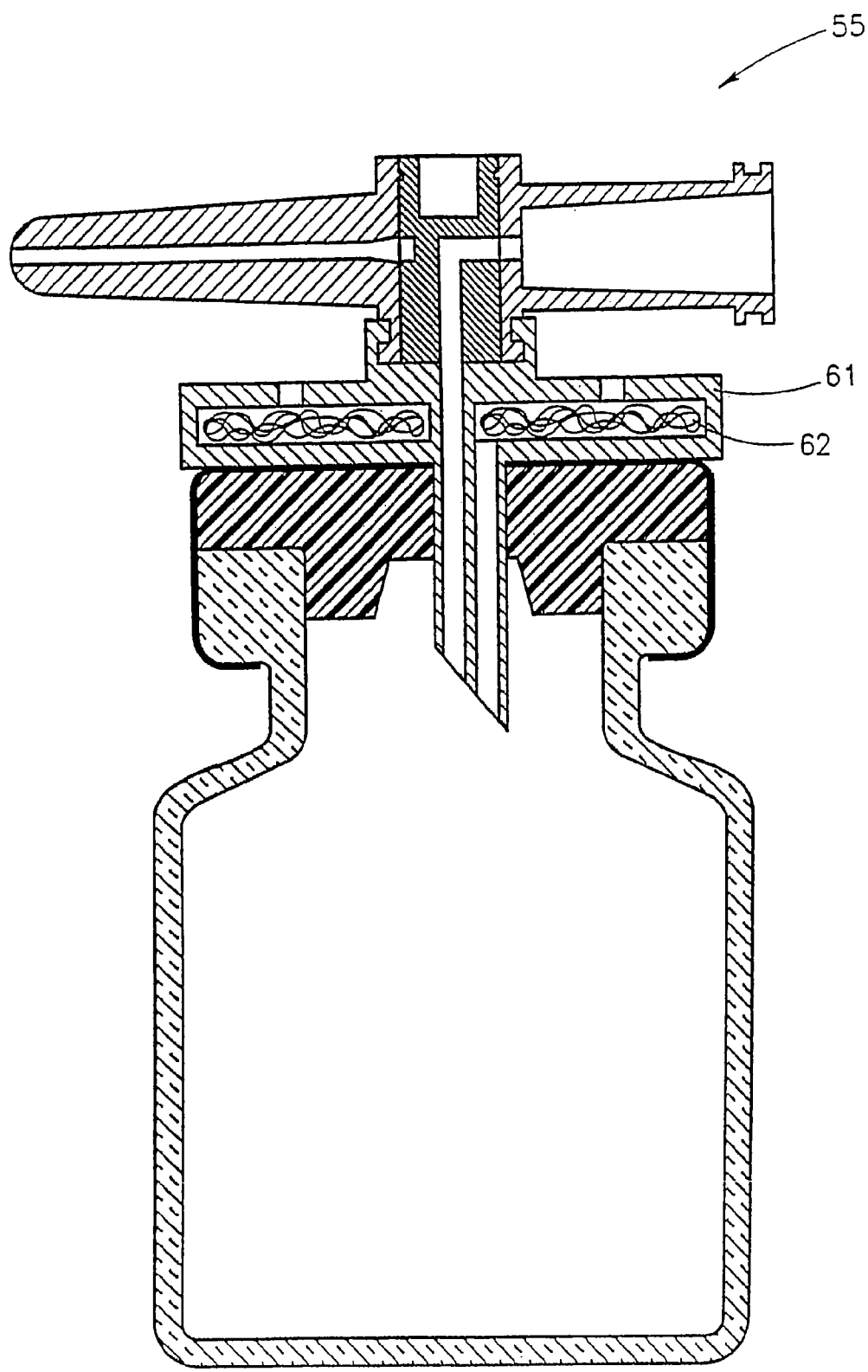
FIG. 19 is a vertical cross sectional view of a fluid control device having an adaptor provided with a lateral cavity for receiving a filter for filtering air venting a vial attached thereto.

FIGS. 17-19 depict other modified fluid control devices, generally-designated 53, 54, 55, constructed and operative in accordance with the teachings of the present invention for enabling fluid flow control between a syringe, a medicinal vessel and a dispensing port. The fluid control device 53, 54 and 55 are similar in construction and operation to the fluid control device 41 and therefore the same reference numerals are used where appropriate. The main difference between the fluid control devices 53, 54, 55 and the fluid control device 41 is that they provide arrangements for venting a vial and, if necessary, for filtering incoming air.

Turning now to FIG. 17, the fluid control device 53 includes an adaptor 56 provided with a venting conduit 58 for venting a vial 28 to the atmosphere in addition to the fluid conduit member 24. The venting conduit 58 is preferably provided with a filter 59 for filtering incoming air. Turning now to FIGS. 18A and 18B, the fluid control device 54 is similar to the fluid control device 53 except that it includes a filter 60 exterior to the adaptor 56. Turning now to FIG. 19, the fluid control device 55 is similar to the fluid control device 53 except that its adaptor 61 includes an integrally formed disposed filter 62.

Figure 20:
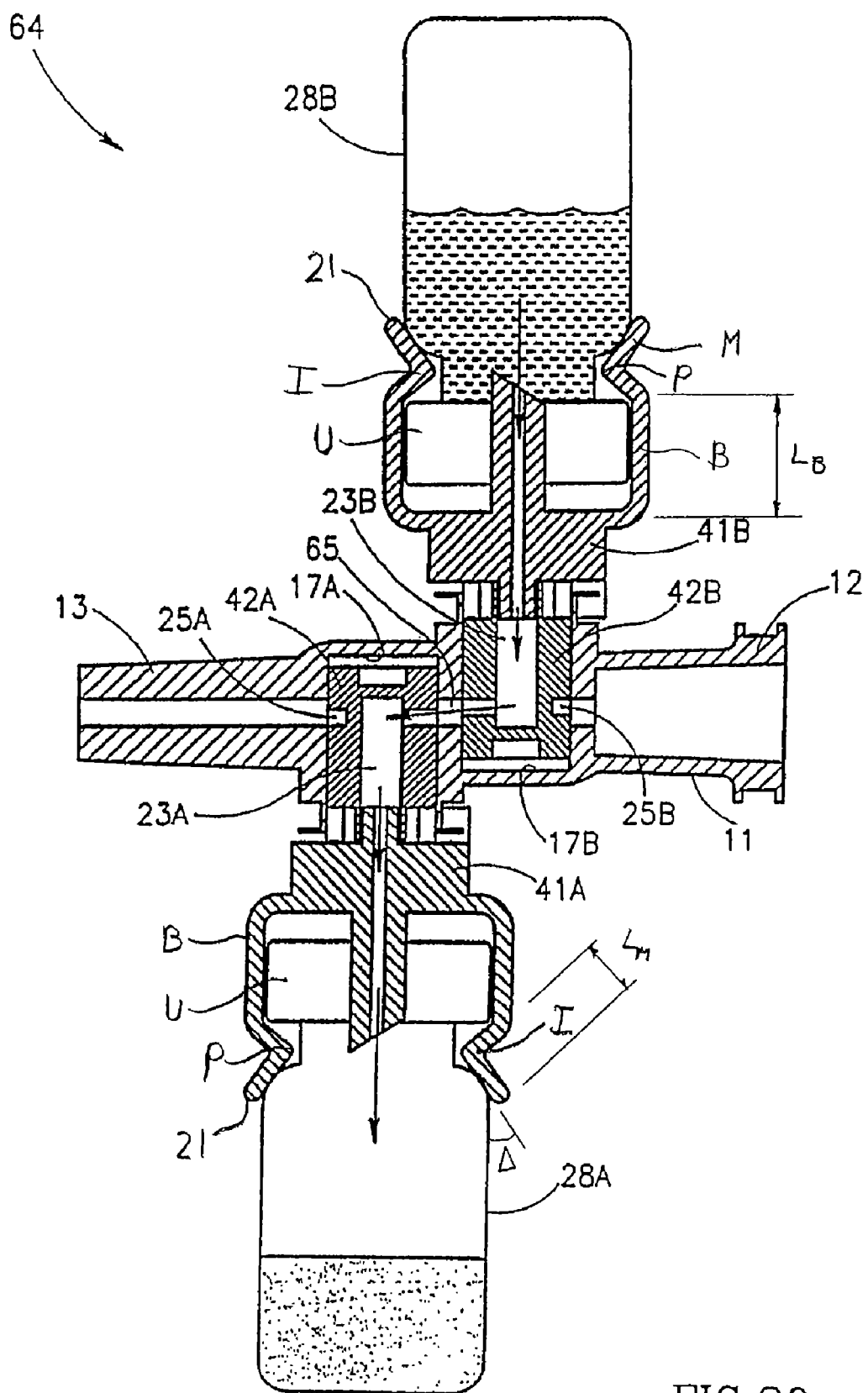
FIG. 20 is a vertical cross sectional view of a fluid control device in a first operative position enabling flow communication between a medicinal vessel containing a powder drug and a medicinal vessel containing a physiological solution for enabling reconstitution of the powder drug.
Figure 21:
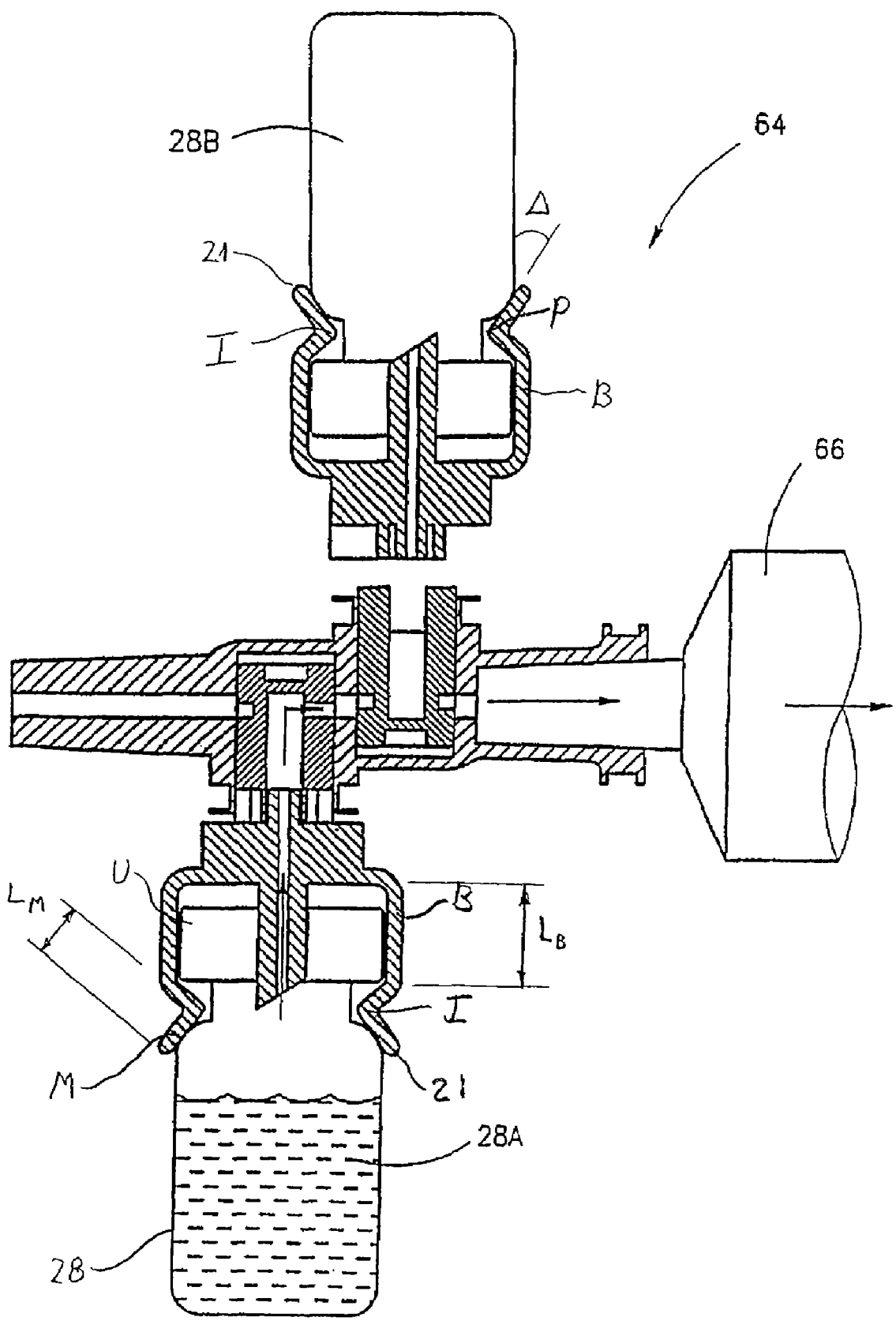
FIG. 21 is a vertical cross sectional view of the fluid control device of FIG. 20 in a second operative position enabling flow communication between the vial containing the reconstituted drug and a syringe.
Figure 22:
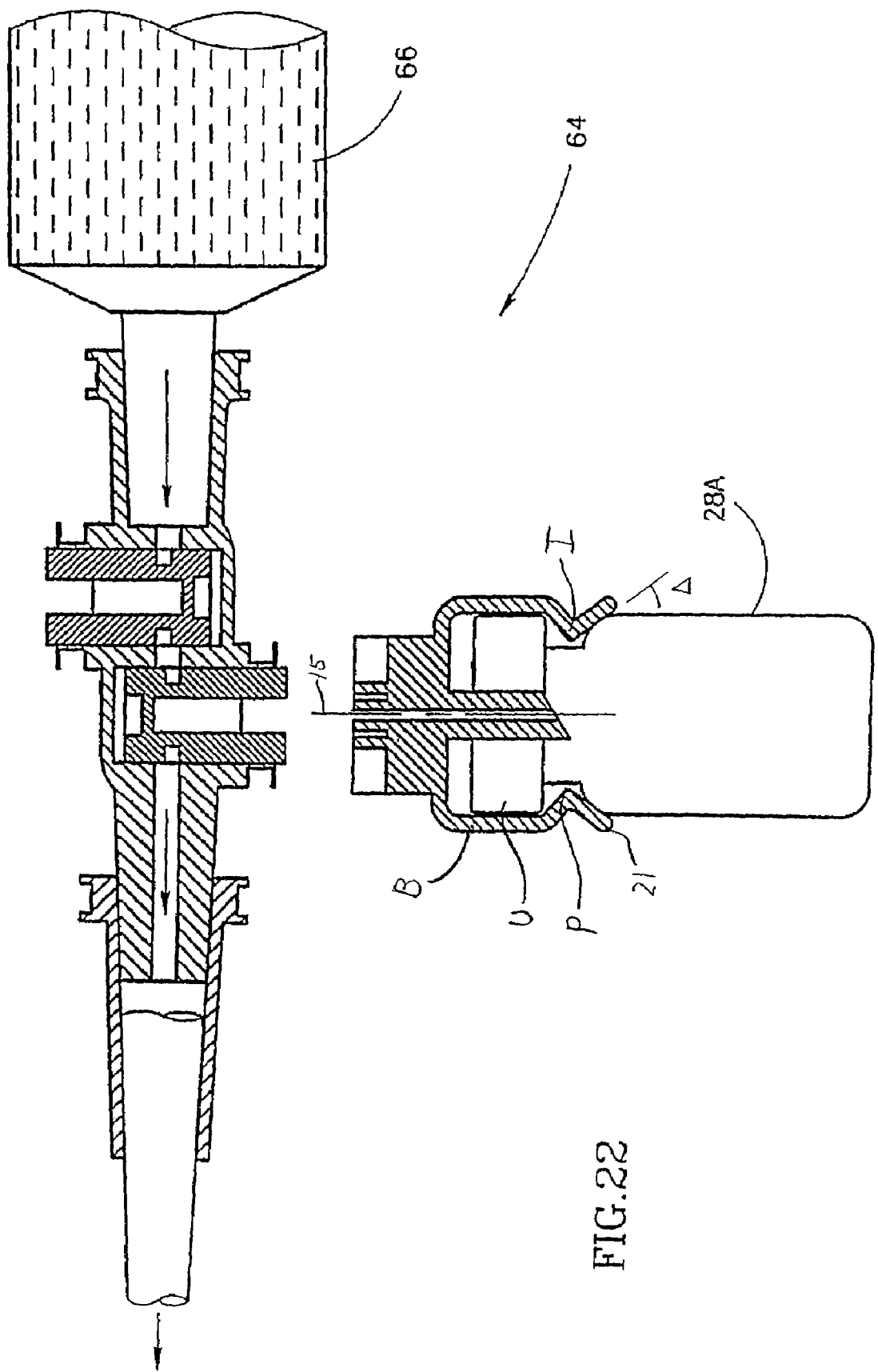
FIG. 22 is a vertical cross sectional view of the fluid control device of FIG. 20 in a third operative position enabling flow communication between the syringe and a dispensing port.

FIGS. 20-22 depict a fluid control device, generally designated 64, for enabling the reconstitution of a powder drug with a physiological solution contained in a medicinal vessel instead of within a pre-filled syringe as required with the fluid control device 10. The fluid control device 64 is similar in construction and operation to the fluid control device 41 and therefore the same reference numerals are used where appropriate.

The main difference between the two fluid control devices 64 and 41 resides in the fact that the former is adapted to be fitted with two medicinal vessels and, as such, its base member 11 is provided with a port 12, a dispensing port 13 and two bores 17A and 17B which are interconnected by a channel 65. As shown, the medicinal vessels are vials 28A and 29B where the vial 28A contains the powdered drug and the vial 28B contains the physiological solution for diluting the powdered drug. As explained in greater detail hereinbelow for the case when the vial 28A has its contents under high vacuum, the sequence and order of the attachment of the vials 28A and 28B to the adapters 41A and 41B is not arbitrary.

In this case, the flow control member 42A has a first flow control position in which its L-shaped flow duct 23A registers in flow communication with the channel 65 and a medicinal vessel attached to its adaptor 41A (see FIGS. 20 and 21) and a second flow control position in which its peripheral groove flow duct 25A registers in flow communication with the channel 65 and the dispensing port 13 (see FIG. 22). In contrast, the flow control member 42B has a first flow control position in which its L-shaped flow duct 23B registers in flow communication with the channel 65 and a medicinal vessel attached to its adaptor 41B (see FIG. 20) and a second flow control position in which its peripheral groove flow duct 25B registers in flow communication with the channel 65 and the port 12 (see FIGS. 21 and 22).

The operation of the fluid control device 64 for the administration of a powder drug provided in the pressurized vial 28A after reconstitution with a physiological solution provided in the vial 28B is now described. First, as shown in FIG. 20, the fluid control device 64 is provided in its first operative position, namely, enabling the flow path between the vials 28A and 28B when they are attached to the base member 11. It should be noted that the vial 28B is attached to the adaptor 41B and thereafter the pressurized vial 28A is attached to the adaptor 41A such that the physiological solution contents of the vial 41B is sucked into the vial 28A. Reconstitution typically requires shaking the fluid control device 64. As shown in FIG. 21, the adaptor 41B together with the vial 28B are then rotated so as to enable their detachment from the base member 11 while at the same time, effecting the rotation of the flow control member 42B so as to enable a flow path between the port 12 and the remaining vial 28A. A syringe 66 is inserted into the port 12 and, after inversion of the fluid control device 64 such that the vial 28 containing the reconstituted drug assumes an upward position, the syringe 66 is aspirated to draw the contents of the vial 28A therein. Thereafter, as shown in FIG. 22, the adaptor 41A together with the vial 28A are rotated so as to enable their detachment from the base member 11 while, at the same time, effecting the rotation of the flow control member 42A so as to enable a flow path between the syringe 66 and the dispensing port 13. Finally, in this position, the syringe 66 is actuated so as to express the drug for its administration to a patient via the dispensing port 13. Finally in this position, the syringe 66 is actuated so as to express the drug for its administration to a patient via the dispensing port 13.

Figure 23:
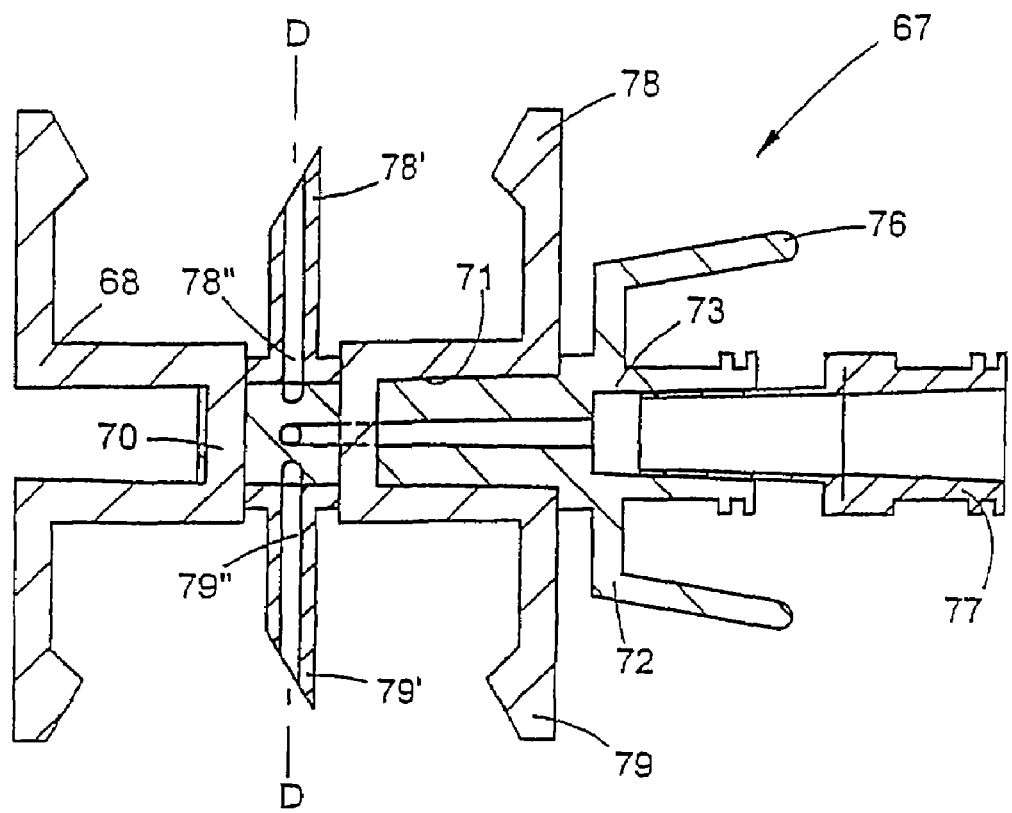
FIG. 23 is a longitudinal cross sectional view of a fluid control device for use with a syringe and a pair of medicinal vessels.
Figure 24:
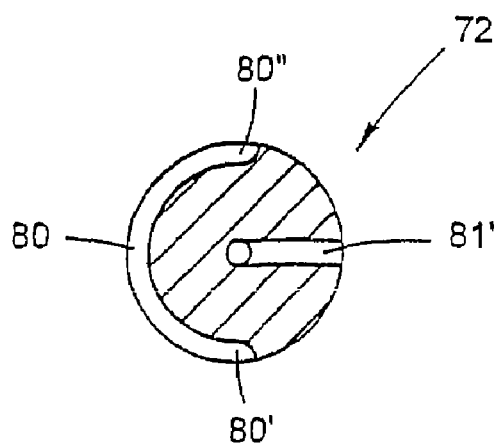
FIG. 24 is a horizontal cross section sectional view, of the flow control member of the fluid control device of FIG. 23 along line D-D.
Figure 25:
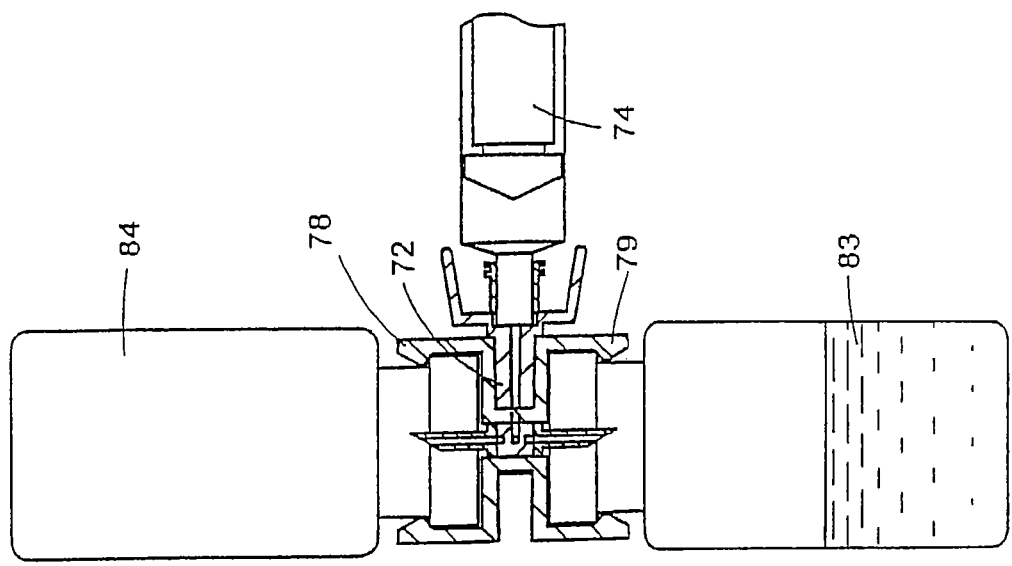
FIG. 25 shows a series of steps (FIGS. 25A-25F) depicting the operation of the fluid control device of FIG. 23.
Figure 25:
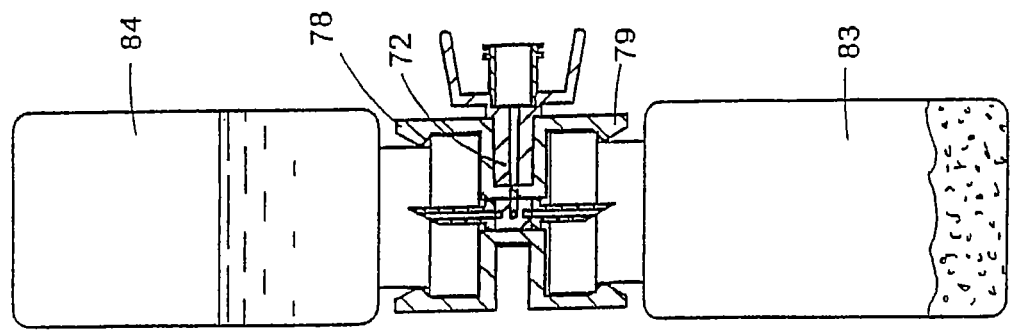
Figure 25:
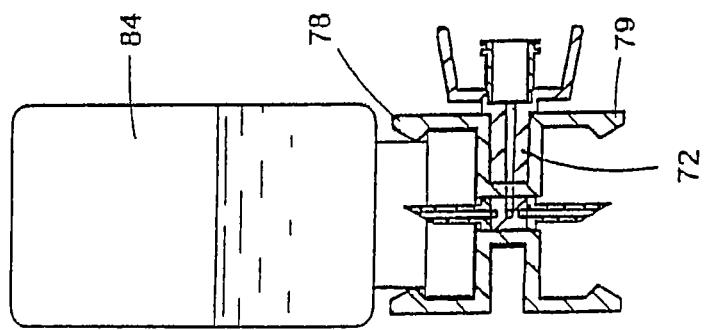
Figure 25:
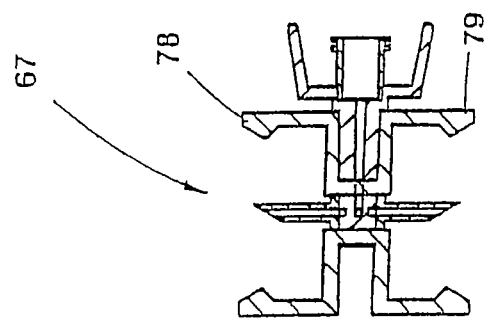

FIGS. 23-25 depicts a fluid control device 67 allowing the preparation of a drug by the mixing between a first substance contained in a first medicinal vessel and a second substance contained in a second medicinal vessel and thereafter the transfer of the drug to a dispensing tool, namely, a syringe.

The fluid control device 67 includes a base member 68 having a generally tubular intermediate portion 70 defining a lumen 71 in which a flow control member 72 is rotatably inserted. The flow control member 72 has a port 73 for receiving a dispensing tool typically, a syringe 74 (see FIG. 25). The port 73 is preferably fashioned as a female luer connector. The flow control member 72 also has integrally formed handles 76 for enabling a manual rotating thereof. As shown, a filter 77 can also be deployed within the port 73 for filtering a drug on its aspiration into a syringe 74.

The base member 68 includes two adapters 78 and 79 which are adapted for the attachment thereto of medicinal vessels. In this case, the adapters 78 and 79 are adapted for the attachment thereto of vials and, as such, they include respective co-axial fluid conduit members 78' and 79' fashioned as piercing tools for puncturing the vials' rubber stoppers. The fluid conduit members 78' and 79' have respective internal apertures 78" and 79".

The flow control member 72 is rotatably mounted for enabling either, in a first flow control position, a flow path between vials attached to the adapters 78 and 79 or, in a second flow control position, a flow path between a syringe and one of the vials. As such, in a similar manner to the flow control member 20' (see FIGS. 3 and 4), flow control member 72 includes two flow ducts as follows: A first flow duct 80 in the form of a peripheral groove slightly longer than semi-circular having end portions 80' and 80" for registration with the interior apertures 78" and 79" so as to enable a flow path between the interiors of vials when attached to the adapters 78 and 79 and a second flow duct 82 in the form of an L-shaped channel having a radial aperture 82' for registration with the interior opening 71' and an axial outlet port 82" so as to enable a flow path between a vial attached to one of the adapters 78 and 79 and a syringe inserted in the port 77.

The operation of the fluid control device 67 is now described with reference to the steps depicted in FIG. 25 for the case that a vial 83 contains a dried drug, e.g. a powder, a crystalline material, a lyophilizate, etc., stored under a high vacuum and a vial 84 contains a physiological solution. As explained in greater detail hereinbelow for the case when the vial 83 has its contents under a high vacuum, the sequence of attachment of the vials 83 and 84 to the adapters 78 and 79 is not arbitrary.

The fluid control device 67 is typically provided in a hermetically sealed package with its flow control member 72 set so as to enable the flow path between flow conduit members 78' and 79' by means of the ends 80' and 80" of its semi-circular groove 80 registering with their interior openings 78" and 79" (FIG. 25A). The vial 84 containing the diluent solution is attached to the adaptor 78 (FIG. 25B), the action of attachment puncturing its rubber stopper and thereafter the vial 83 containing the dried drug is attached to the adaptor 79 (FIG. 25C) thereby sucking the diluent solution therein once its rubber stopper is punctured (FIG. 25D). The contents of the vial 83 are then shaken so as to mix the diluent solution with the dried drug.

The syringe 74 is inserted into the port 73 (FIG. 25D) and the flow control member 72 is rotated through a quarter turn relative to the base member 11 such that the flow path between the syringe 74 and the vial 83 is enabled. (FIG. 25E). The fluid control device 67 is then inverted (FIG. 25F) and the syringe 74 is aspirated so as to draw the reconstituted drug therein, the medicinal preparation passing through a deployed filter 77, if any, thereby becoming particle free for administration to a patient.

Figure 26:
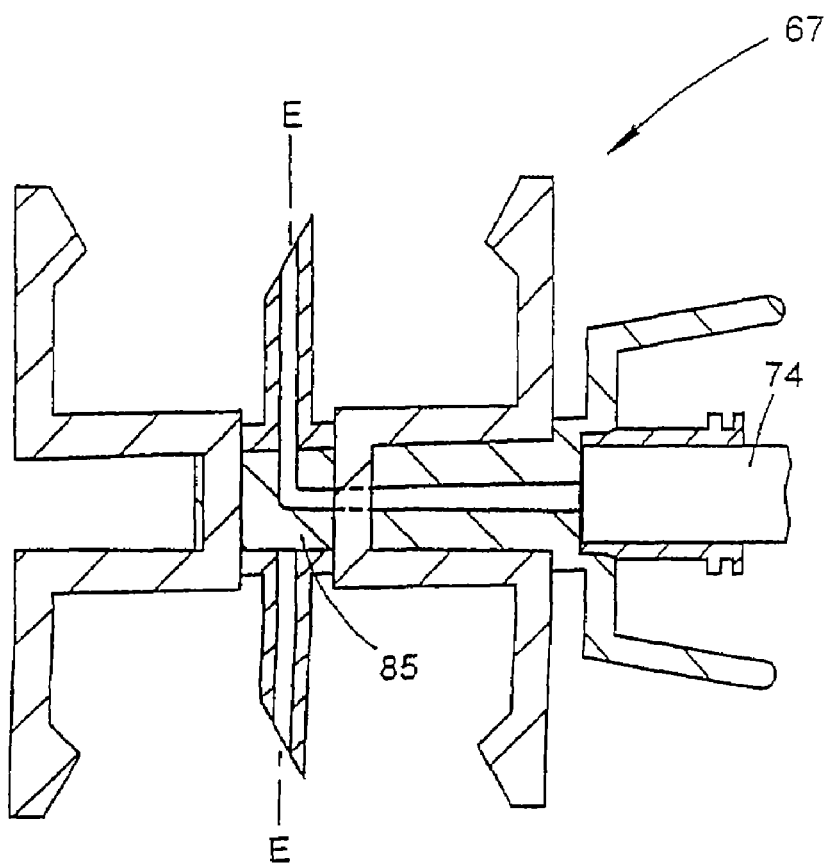
FIG. 26 is a longitudinal cross sectional view of the fluid control device of FIG. 23 with a modified flow control member.
Figure 27:
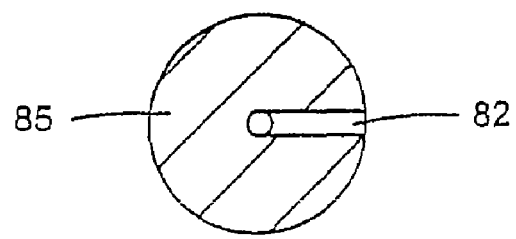
FIG. 27 is a horizontal cross sectional view of the flow control member of FIG. 26 along line E-E in FIG. 26.

FIGS. 26 and 27 depict the fluid control device 67 with a modified flow control member 85 having just the L-shaped flow duct 82, thereby requiring that it be rotated through a one hundred eighty degree (180°) turn for switching between its two flow control positions, the first flow control position being between a syringe inserted in the port 73 and a first medicinal vessel while the second flow control position being between a syringe inserted in the port 73 and a second medicinal vessel.

The difference between the flow control member 85 and 72 being that a fluid control device 67 fitted with the former can be employed with medicinal vessels in which their contents are under a low vacuum or no vacuum, thereby requiring user intervention to perform the mixing of the powder drug with the physiological solution. In particular, the flow control member 85 is suitable for use with a fluid control device 67 having an adaptor suitable for connection to an IV bag such that on setting the flow control member 85 in its first operative position, the syringe 74 is aspirated so as to introduce a predetermined volume of diluent solution therein. Thereafter, on setting the flow control member 85 into its second operative position, the syringe 74 is actuated so as to introduce the diluent solution into a second medicinal vessel containing the drug to be reconstituted. After mixing of the drug with the diluent solution, the syringe 74 is aspirated a second time so as to introduce the medicinal liquid therein at which time the syringe 74 is removed for administration of the drug to a patient. In this fashion, such a fluid control device can be used a number of times with one or more medicinal vessels.

Figure 28:
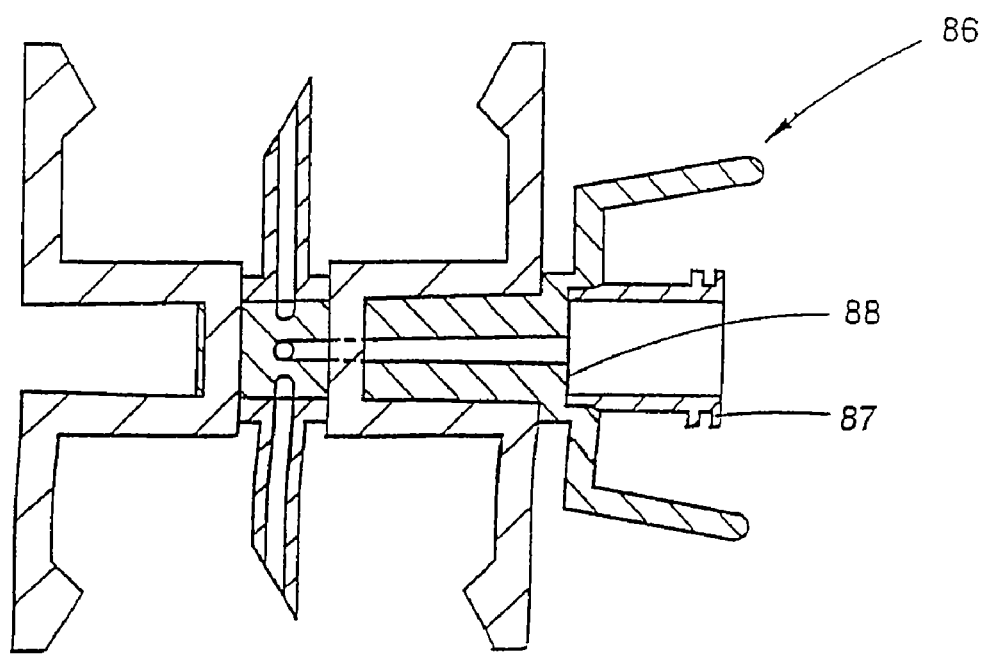
FIG. 28 is a longitudinal cross sectional view of a modified fluid control device of FIG. 23 with an in-line filter.
Figure 29:
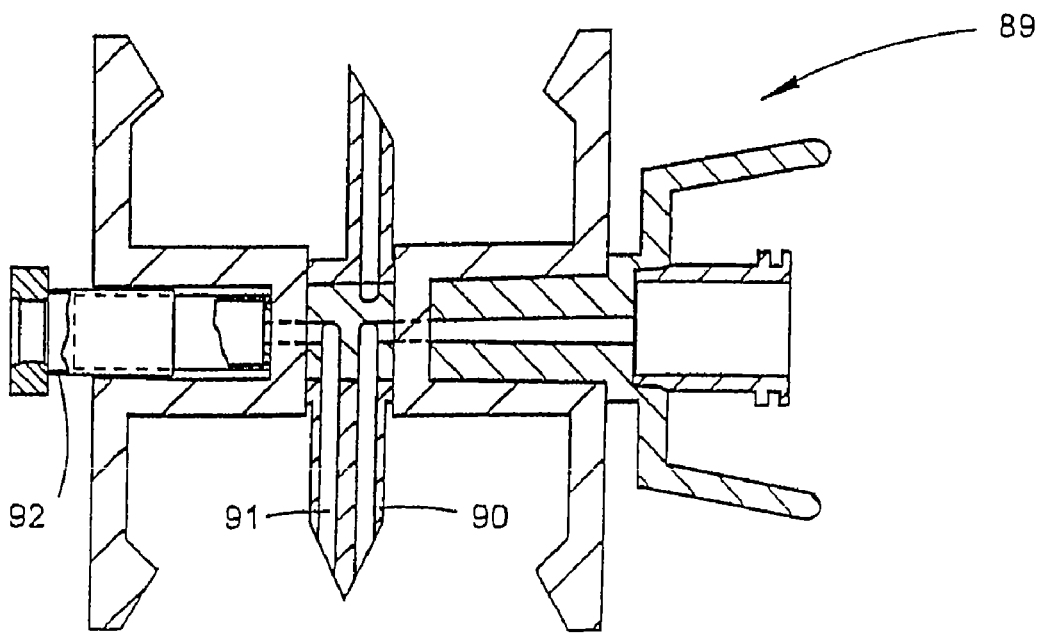
FIG. 29 is a longitudinal cross sectional view of a fluid control device with a modified adaptor enabling venting of a medicinal vessel attached thereto fitted with a hydrophobic filter.

FIG. 28 depicts a fluid control device 86 with a port 87 provided with an integral in-line filter 88, thereby obviating the need for a filter 77. FIG. 29 depicts a fluid control device 89 with a modified adaptor 90 having a vent conduit 91 for venting the vial attached thereto provided with a hydrophobic filter 92 so as to prevent wastage of the mixed drug when the fluid control device 89 is manipulated into the position shown in FIG. 25F.

Referring next to FIGS. 30 through 35, another form of the adapter component of the invention is there shown. This novel adapter component, which is generally designated in FIG. 30 by the number 100, comprises a top wall 102, a hollow cannula 104 that is connected to top wall 102 and depends therefrom and a resiliently deformable skirt 106 that is connected to top wall 102. The hollow cannula 104 includes a puncturing tip 104a positioned along the longitudinal axis 15 of the adapter 100. As indicated in FIG. 30, a portion of skirt 106 extends downwardly from top wall 102 and is adapted to telescopically receive the generally cylindrically shaped upper portion of a bottle such as bottle 28 (FIG. 1).

The skirt 106 of the adapter component 100 is of a unique configuration and includes a generally cylindrical body portion 106a, an angularly outwardly extending marginal portion 106b and an angularly inwardly extending intermediate portion 106c that is disposed between the body portion 106a and the marginal portion 106b. The intermediate portion 106c comprises a circumferentially extending protuberance 106d that functions to releasably grip the neck portion of bottle 28 or the lower edge of the upper portion U of the vial 28. As in the earlier described adapter constructions, the adapter 100 of the present form of the invention is provided with a plurality of circumferentially spaced slits 110 that define flex members 111 therebetween. The slits 110 and flex members 111 permit the skirt portion to flex sufficiently to enable it to be expeditiously snapped over the neck portion of the bottle or vial 28 such that the protuberances 106d engage the lower edge of the upper portion U of the vial 28 in an engaged position. The outwardly extending marginal portion 106b includes a distal end 107 and extends from the intermediate portion 106c at a guiding angle Δ. The outwardly extending marginal portion 106b has a length $L_M$ that is at least one-third (⅓) the length $L_B$ of the generally cylindrical body portion 106a.

Figure 32:
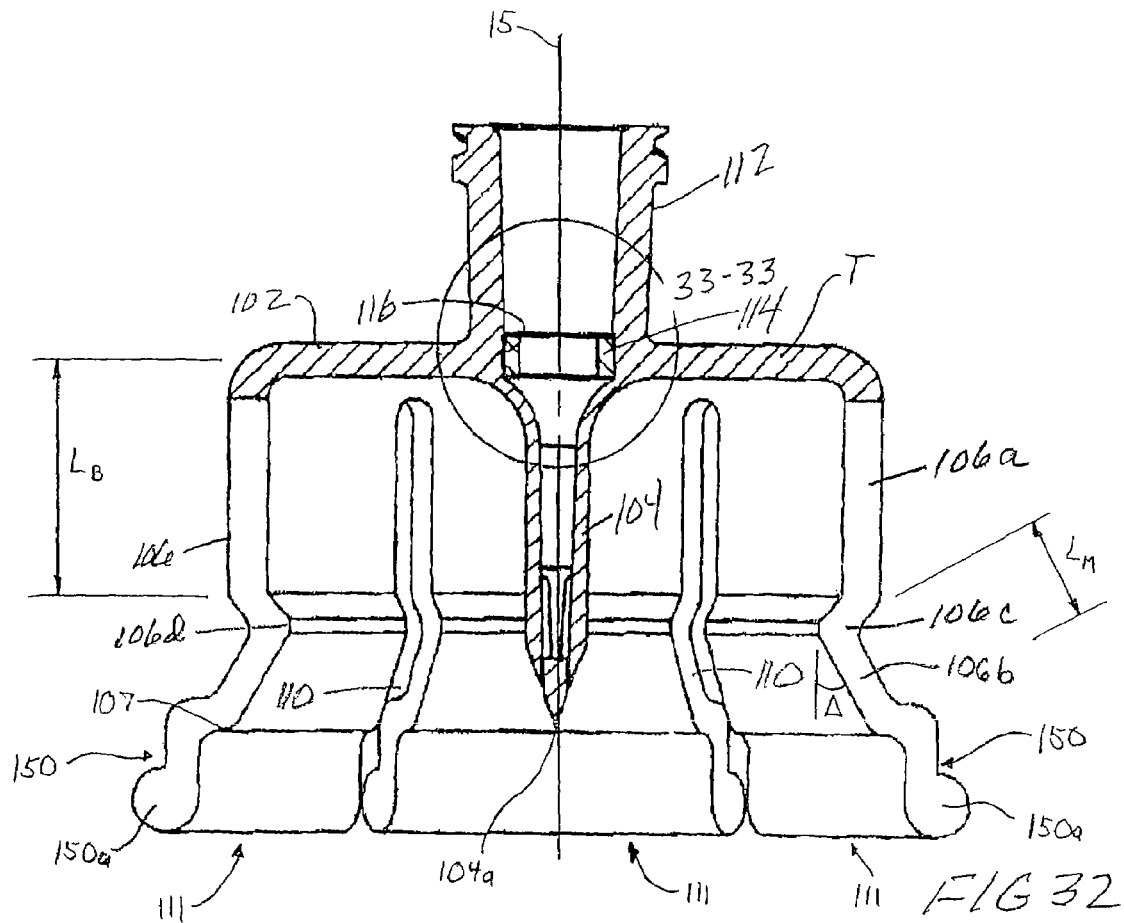
FIG. 32 is a side-elevational view partly in cross section similar to FIG. 30 but showing the filter element disposed within a specially configured cavity formed at the base of the upper connector portion of the adapter that extends from the top wall thereof.
Figure 33:
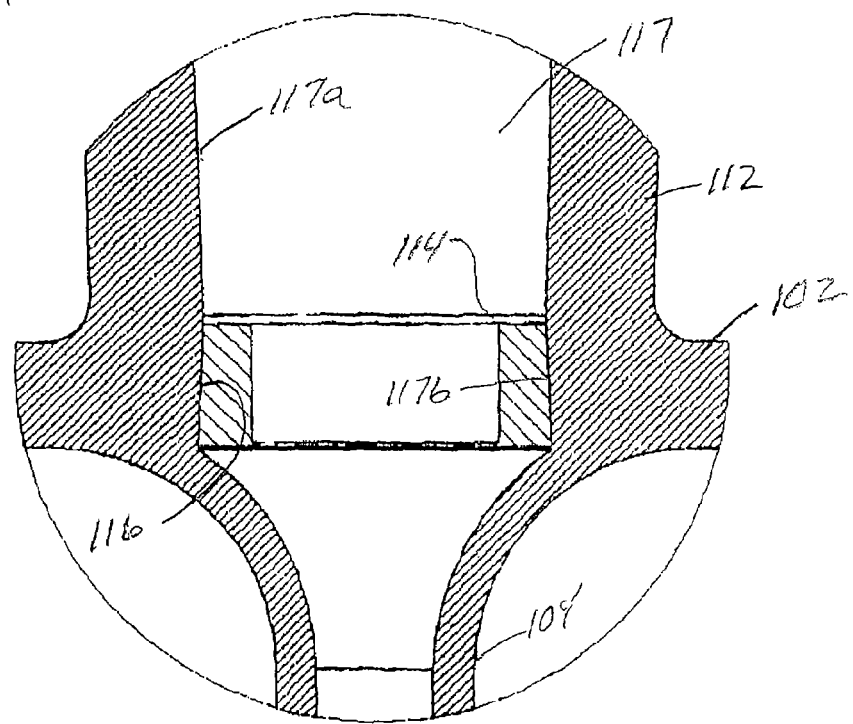
FIG. 33 is a greatly enlarged, cross-sectional view of the area designated as 33-33 of FIG. 32 better illustrating the configuration of the filter and the filter retaining cavity.
Figure 34:
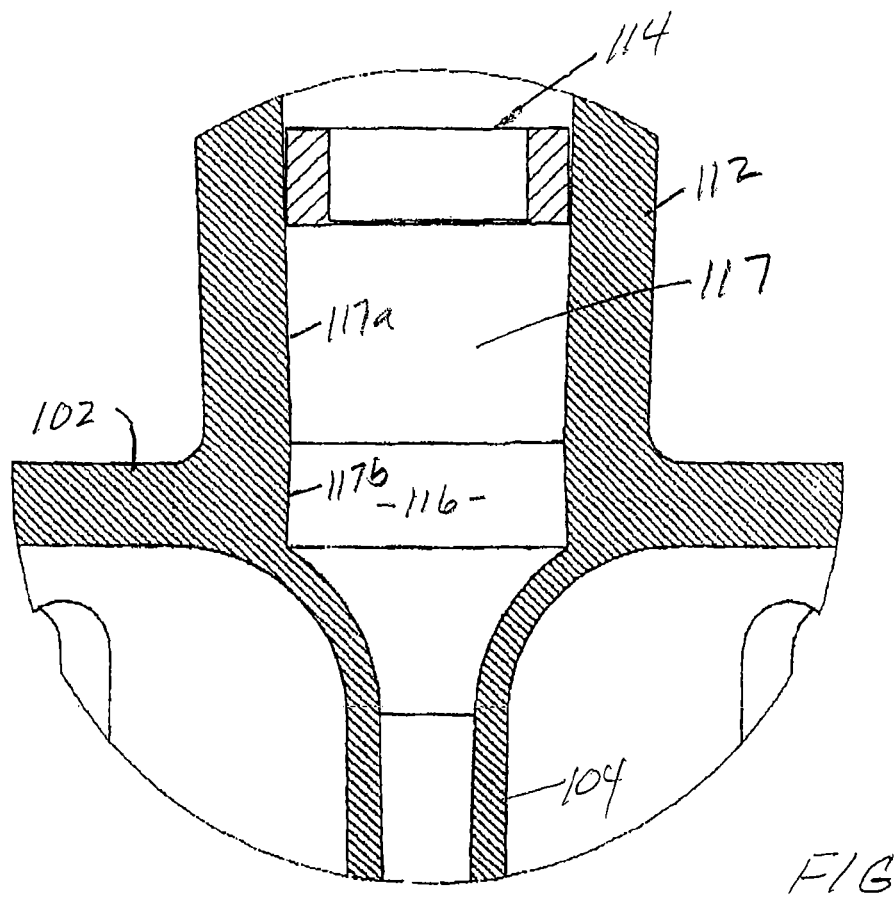
FIG. 34 is a cross-sectional view similar to FIG. 33, but showing the filter element in the process of being inserted into the connector portion.
Figure 35:
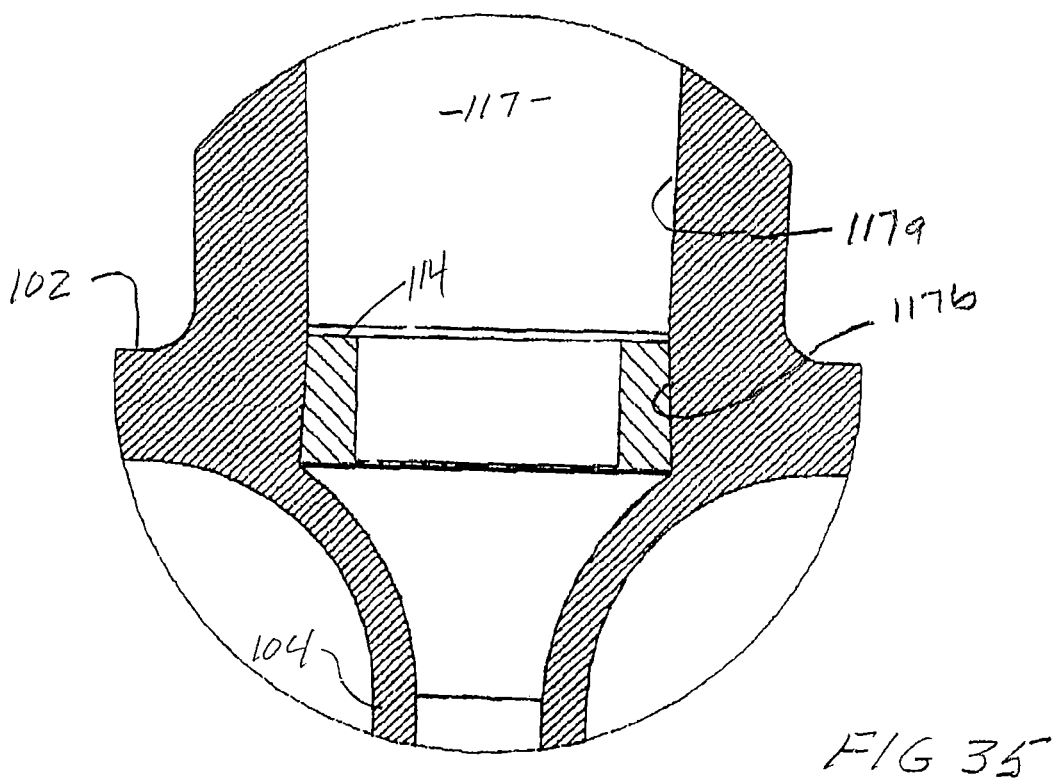
FIG. 35 is a cross-sectional view similar to FIG. 34, but showing the filter element seated within the filter receiving cavity.

Adapter 100 also includes a connector portion 112 that is connected to top wall 102 and extends outwardly therefrom in the manner shown in FIGS. 30 and 32. Connector portion 112 functions to enable a length of tubing to be connected proximate one end thereof to the adapter. Connector portion 112 also functions to house filter means for filtering the liquid as it is removed from bottle 28. This important filter means here comprises an in-line, disc-type filter 114 that is uniquely held in position within a reverse taper socket 116 that is formed within connector portion 112 (see also FIGS. 32 and 33).

Referring particularly to FIG. 31, it is to be noted that connector 112 is provided with a tapered bore 117, the upper wall portion 117a of which tapers inwardly at an angle X relative to vertical V. However, the lower wall portion 117b of the bore tapers outwardly relative to vertical V at an angle of Y, so as to define a reverse taper that forms the boundary of socket 116 within which filter 114 is secured in the manner shown in FIGS. 32 and 33. With this novel construction, the filter will be held securely in place within the cavity in the manner best seen in FIG. 33.

Figure 36:
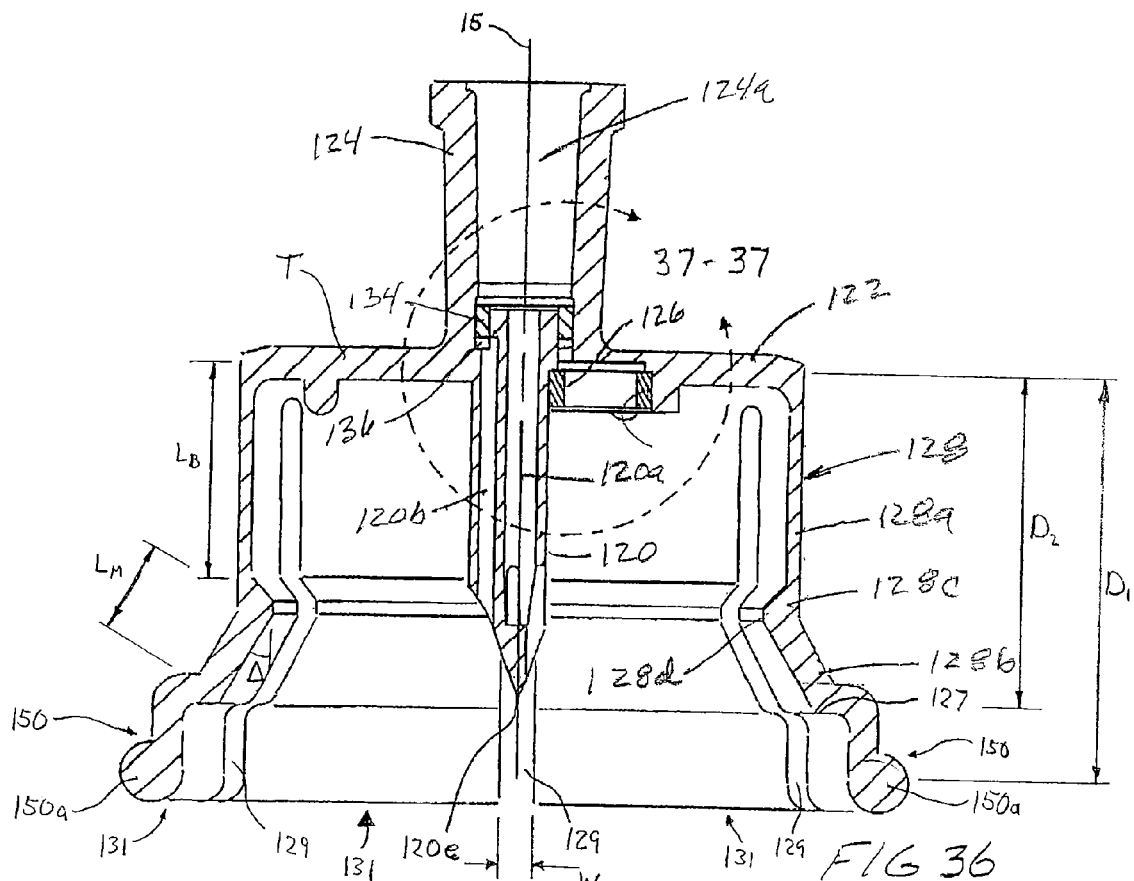
FIG. 36 is a side-elevational, cross-sectional view of still another form of the adapter component of the present invention.
Figure 37:
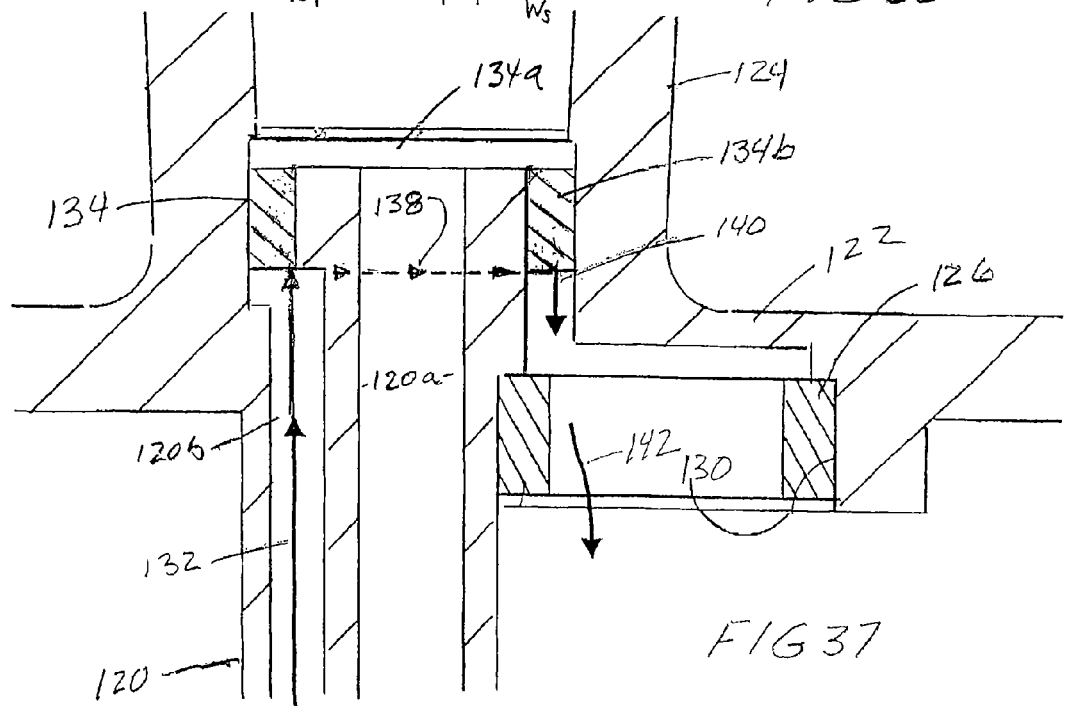
FIG. 37 is a greatly enlarged cross-sectional view of the area designated as 37-37 in FIG. 36.

Referring to FIGS. 36 and 37, still another form of the adapter component of the present invention is there shown. This adapter component is similar in some respects to adapter component 100. However, it is to be noted that the cannula 120 that depends from top wall 122 of the adapter components has a first lumen 120a that defines a fluid flow path between the interior of the bottle and the flow passageway 124a of a connector 124 that extends upwardly from top wall 122. Cannula 120 also has a second lumen 120b that defines a venting passageway for permitting the passage of air between the interior of the drug bottle or vial and the exterior thereof via appropriate air filtering means. This air filtering means here comprises a conventional microporous filter 126 which permits venting of gases through the filter but prevents the passage therethrough of liquid and particles of selected sizes. The cannula 120 includes a puncturing tip 120e that is positioned along the longitudinal axis 15.

As in the earlier described embodiments, this latter form of adapter component is constructed of plastic and includes a skirt 128 that extends from top wall 122. The skirt 128 has a generally cylindrically shaped portion 128a and an outwardly extending marginal portion 128b. The skirt 128 also has an intermediate portion 128c that includes a circumferentially extending protuberance 128d that functions in the manner previously described to releasably grip the neck portion of the vial or drug bottle 28. The outwardly extending marginal portion 128b includes a distal end 127 and extends from the intermediate portion 128c at a guiding angle Δ. The skirt 128 includes slits 129 that define flex members 131 therebetween. The outwardly extending marginal portion 128b has a length $L_M$ that is at least one-third (⅓) the length $L_B$ of the generally cylindrical body portion 128a.

Referring to FIGS. 30, 32 and 36, the flex members 111, 131 of the skirts 106, 128 of the adaptors 100 include a bead 150 extending from the distal ends 107, 127 of the marginal portions 106b, 128b. The bead 150 has a terminal end 150a spaced from the marginal portion 106b, 128b and from the distal end 107, 127 of the flex members 111, 131. The terminal end 150a has a generally circular cross-section. The skirts 106, 128 include the top wall T and the terminal end 150a is located a first distance D1 from the top wall T. The puncturing tips 104a, 120e of the cannula 104, 120 are located a second distance D2 from the top wall T. The first distance D1 is greater than the second distance D2 such that user exposure to the puncturing tip 104a, 120e is minimized.

Referring to FIGS. 1, 2, 4, 7, 9 and 36, the slits CS, 129 in the skirts S, 128 have a generally uniform width $W_S$ along the entire length of the slits CS, 129.

As indicated in the drawings, filter 126 is mounted within a chamber 130 formed in top wall 122 of the adapter. With this construction, during the vial filling step, displaced air can flow from the interior of the bottle through lumen 120b in the direction of the arrow 132 toward a disk filter 134, around lumen 120a, through a passageway 136 in the direction of arrow 138 (FIG. 37). The membrane portion 134a of disc filter 134 permits the flow of air therethrough, while the blocking ring portion 134b prevents the flow of air therethrough. After reaching the ring portion of the disc filter, the air flows in the direction of arrows 138, 140, and 142 to atmosphere via air filter 126. During the infusion step, when the medicinal fluid is being removed from the bottle and administered to the patient via passageways 120a and 124a, replacement air can flow through these same passageways from atmosphere to the interior of the vial with the replacement air being appropriately filtered by the filters carried by the adapter component.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A combination fluid transfer device and fluid device for accommodating flow of fluid from a vial to a vessel, the vial having an outermost peripheral portion, the combination comprising:

a male connector extending generally perpendicularly from a top wall of the fluid transfer device;

a grip extending generally perpendicularly from the top wall of the fluid transfer device and at least partially circumferentially surrounding the male connector;

a skirt extending generally perpendicularly from the top wall in an opposite direction from the male connector, the skirt telescopically receiving the outermost peripheral portion of the vial, the skirt including a terminal end located at a first distance from the top wall;

a cannula extending generally perpendicularly from a central location of the top wall opposite the male connector, the cannula including a puncturing tip located at a second distance from the top wall, the first distance being greater than the second distance;

a flow duct extending between the male connector and the cannula; and a female connector associated with the fluid device, the male connector releasably, surroundingly insertable into the female connector, the grip releasably couplable to an outer surface of the female connector, the female connector being in fluid communication with the vessel and the flow duct.

2. The combination of claim 1 wherein the vessel is comprised of a syringe that is in fluid communication with the vial through the flow duct in an engaged position of the vial, fluid transfer device and syringe.

3. The combination of claim 1 wherein the skirt includes a first flex member and a second flex member, the first flex member being diametrically opposed to the second flex member, the first flex member including a first protuberance and the second flex member including a second protuberance, the first and second protuberances engage the vial in an engaged position.

* * * * *